(12) United States Patent
Gray et al.

(10) Patent No.: US 8,501,406 B1
(45) Date of Patent: Aug. 6, 2013

(54) SELECTIVELY FUNCTIONALIZED ARRAYS

(75) Inventors: Jeremy Gray, San Francisco, CA (US); Ronald Cicero, Palo Alto, CA (US); Gregory Kearns, San Mateo, CA (US); Stephen Dudek, San Francisco, CA (US); Natasha Popovich, Menlo Park, CA (US); Robert Sebra, San Francisco, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 408 days.

(21) Appl. No.: 12/797,260

(22) Filed: Jun. 9, 2010

Related U.S. Application Data

(60) Provisional application No. 61/225,507, filed on Jul. 14, 2009.

(51) Int. Cl.
  *C12Q 1/68* (2006.01)
  *C12M 1/00* (2006.01)
  *C12M 1/34* (2006.01)
  *C12M 3/00* (2006.01)

(52) U.S. Cl.
  USPC .... 435/6.1; 435/283.1; 435/287.1; 435/287.2

(58) Field of Classification Search
  USPC ........ 435/6, 6.1, 283.1, 287.1, 287.2; 514/44; 424/482
  See application file for complete search history.

(56) References Cited

U.S. PATENT DOCUMENTS

| | | | |
|---|---|---|---|
| 5,001,050 A | 3/1991 | Blanco et al. | |
| 5,143,854 A | 9/1992 | Pirrung et al. | |
| 5,198,543 A | 3/1993 | Blanco et al. | |
| 5,412,087 A | 5/1995 | McGall et al. | |
| 5,424,186 A | 6/1995 | Fodor et al. | |
| 5,547,839 A | 8/1996 | Dower et al. | |
| 5,576,204 A | 11/1996 | Blanco et al. | |
| 5,624,711 A | 4/1997 | Sundberg et al. | |
| 5,723,584 A | 3/1998 | Schatz | |
| 5,733,651 A | 3/1998 | Wank et al. | |
| RE35,821 E * | 6/1998 | Niki et al. | 430/326 |
| 5,821,058 A | 10/1998 | Smith et al. | |
| 5,851,840 A | 12/1998 | Sluka et al. | |

(Continued)

FOREIGN PATENT DOCUMENTS

| | | |
|---|---|---|
| EP | 1105529 B1 | 9/2005 |
| WO | WO 91/06678 A1 | 5/1991 |

(Continued)

OTHER PUBLICATIONS

CN Office Action dated May 11, 2010 for related application No. CN 200780012053.3.

(Continued)

*Primary Examiner* — Robert T. Crow
(74) *Attorney, Agent, or Firm* — Quine Intellectual Property Law Group, P.C.; Monicia Elrod-Erickson; Robert Reamey

(57) ABSTRACT

Methods, substrates, and devices related to arrays of optical confinements having surfaces with high levels of bias. Substrates having transparent or silica based portions and opaque or reflective portions are treated with 1) a selective passivating agent, that selectively coats the opaque or reflective regions, 2) a functionalizing agent such as a coupling agent, and 3) a selective removal agent, which selectively removes functionalizing agent from the passivated opaque or reflective surfaces.

21 Claims, 11 Drawing Sheets

U.S. PATENT DOCUMENTS

| | | | |
|---|---|---|---|
| 5,874,239 | A | 2/1999 | Schatz |
| 5,919,523 | A | 7/1999 | Sundberg et al. |
| 5,932,433 | A | 8/1999 | Schatz et al. |
| 6,028,025 | A | 2/2000 | Ying et al. |
| 6,210,896 | B1 | 4/2001 | Chan |
| 6,235,488 | B1 | 5/2001 | Tom-Moy et al. |
| 6,265,552 | B1 | 7/2001 | Schatz |
| 6,787,308 | B2 | 9/2004 | Balasubramanian et al. |
| 6,818,395 | B1 | 11/2004 | Quake et al. |
| 6,869,764 | B2 | 3/2005 | Williams et al. |
| 6,887,685 | B1 | 5/2005 | Walke et al. |
| 6,917,726 | B2 | 7/2005 | Levene et al. |
| 6,982,146 | B1 | 1/2006 | Schneider et al. |
| 6,991,726 | B2 | 1/2006 | St. Germain |
| 7,013,054 | B2 | 3/2006 | Levene et al. |
| 7,033,762 | B2 | 4/2006 | Nelson et al. |
| 7,033,764 | B2 | 4/2006 | Korlach et al. |
| 7,052,847 | B2 | 5/2006 | Korlach et al. |
| 7,056,661 | B2 | 6/2006 | Korlach et al. |
| 7,056,676 | B2 | 6/2006 | Korlach et al. |
| 7,064,197 | B1 | 6/2006 | Rabbani et al. |
| 7,170,050 | B2 | 1/2007 | Turner et al. |
| 7,302,146 | B2 | 11/2007 | Turner et al. |
| 7,315,019 | B2 | 1/2008 | Turner et al. |
| 7,476,503 | B2 | 1/2009 | Turner et al. |
| 7,486,865 | B2 | 2/2009 | Foquet et al. |
| 7,763,423 | B2 | 7/2010 | Roitman et al. |
| 7,907,800 | B2 | 3/2011 | Foquet et al. |
| 7,931,867 | B2 | 4/2011 | Korlach |
| 7,932,035 | B2 | 4/2011 | Korlach |
| 7,935,310 | B2 | 5/2011 | Korlach |
| 7,993,891 | B2 | 8/2011 | Roitman et al. |
| 8,137,942 | B2 | 3/2012 | Roitman et al. |
| 8,193,123 | B2 | 6/2012 | Rank et al. |
| 2002/0128234 | A1 | 9/2002 | Hubbell et al. |
| 2002/0137053 | A1 | 9/2002 | Ault-Riche et al. |
| 2003/0044781 | A1 | 3/2003 | Korlach et al. |
| 2003/0174992 | A1 | 9/2003 | Levene et al. |
| 2003/0186276 | A1 | 10/2003 | Odreda |
| 2003/0186914 | A1* | 10/2003 | Hofer et al. ............... 514/44 |
| 2003/0190647 | A1 | 10/2003 | Odreda |
| 2003/0194740 | A1 | 10/2003 | Williams |
| 2003/0215862 | A1 | 11/2003 | Parce et al. |
| 2004/0048301 | A1 | 3/2004 | Sood et al. |
| 2004/0180147 | A1 | 9/2004 | Parikh et al. |
| 2004/0224319 | A1 | 11/2004 | Sood et al. |
| 2004/0234964 | A1 | 11/2004 | Cole et al. |
| 2005/0131219 | A1 | 6/2005 | Urdea et al. |
| 2005/0148027 | A1 | 7/2005 | Pirrung et al. |
| 2005/0208557 | A1 | 9/2005 | Korlach et al. |
| 2005/0233473 | A1 | 10/2005 | Cicero et al. |
| 2006/0177855 | A1 | 8/2006 | Utermohlen et al. |
| 2007/0036511 | A1 | 2/2007 | Lundquist et al. |
| 2007/0077564 | A1 | 4/2007 | Roitman et al. |
| 2007/0128133 | A1 | 6/2007 | Eid et al. |
| 2007/0134128 | A1 | 6/2007 | Korlach |
| 2007/0196846 | A1 | 8/2007 | Hanzel et al. |
| 2008/0032301 | A1 | 2/2008 | Rank et al. |
| 2008/0156974 | A1 | 7/2008 | Turner et al. |
| 2008/0161194 | A1 | 7/2008 | Turner et al. |
| 2008/0161195 | A1 | 7/2008 | Turner et al. |
| 2008/0176761 | A1 | 7/2008 | Menchen et al. |
| 2008/0176769 | A1 | 7/2008 | Rank et al. |
| 2009/0061429 | A1 | 3/2009 | Roitman et al. |
| 2009/0129980 | A1 | 5/2009 | Lawson et al. |
| 2010/0099100 | A1 | 4/2010 | Zaccarin et al. |
| 2010/0261158 | A1 | 10/2010 | Nordman et al. |
| 2011/0117637 | A1 | 5/2011 | Gray et al. |
| 2011/0222179 | A1 | 9/2011 | Monadgemi |
| 2011/0257040 | A1 | 10/2011 | Turner et al. |

FOREIGN PATENT DOCUMENTS

| | | | |
|---|---|---|---|
| WO | WO 96/27025 | A1 | 9/1996 |
| WO | WO 99/05315 | A2 | 2/1999 |
| WO | WO 00/36152 | A1 | 6/2000 |
| WO | WO 00/53805 | A1 | 9/2000 |
| WO | WO 01/16375 | A2 | 3/2001 |
| WO | WO 2004/017042 | A2 | 2/2004 |
| WO | WO 2004/055160 | A2 | 7/2004 |
| WO | WO 2005/084367 | A2 | 9/2005 |
| WO | WO 2007/064597 | A2 | 6/2007 |
| WO | WO 2007/075873 | A2 | 7/2007 |

OTHER PUBLICATIONS

CN Office Action dated Nov. 4, 2010 for related application No. CN 200780012053.3.

CN Office Action dated Apr. 25, 2011 for related application No. CN 200780012053.3.

CN Office Action dated Oct. 26, 2011 for related application No. CN 200780012053.3.

EP communication under Rule 71(3) EPC dated Jan. 12, 2011 from corresponding EP application No. 07754529.1.

EP Examination Report dated Apr. 14, 2010 for related application No. EP 07754529.1.

EP Examination Report dated Sep. 21, 2009 for related application No. EP 07754529.1.

EP summons to oral proceedings dated Dec. 7, 2011 from corresponding EP application No. 07754529.1.

Extended EP search report dated Jun. 17, 2009 for related application No. EP 07754529.1.

International Preliminary Report on Patentability dated Oct. 9, 2008 for related application No. PCT/US2007/008019.

International Search Report and Written Opinion dated Sep. 10, 2008 for related application No. PCT/US2007/008019.

Bakiamoh and Blanchard (2001) "Surface second harmonic generation from asymmetric multilayer assemblies: gaining insight into layer-dependent order," Langmuir, 17:3438-3446.

Blonder et al. (1997) "Application of a Nitrospiropyran-FAD-Reconstituted Glucose Oxidase and Charged Electron Mediators as Optobioelectronic Assemblies for the Amperometric Transduction of Recorded Optical Signals: Control of the "On"—"Off" Direction of the Photoswitch," JACS, 119(49):11747-11757.

Blonder et al. (1997) "Development of Amperometric and Microgravimetric Immunosensors and Reversible Immunosensors Using Antigen and Photoisomerizable Antigen Monolayer Electrodes," JACS, 119(43):10467-10478.

Bruckbauer et al. (2004) "An addressable antibody nanoarray produced on a nanostructured surface," J. Am. Chem. Soc., 126(21):6508-6509.

Brukman et al. (2006) "Nanotribological properties of alkanephosphonic acid self-assembled monolayers on aluminum oxide: effects of fluorination and substrate crystallinity," Langmuir, 22(9):3988-3998.

Danelon et al. (2006) "Cell membranes suspended across nanoaperture arrays," Langmuir,22(1):22-25.

Decher (1997) "Fuzzy, nanoassemblies: toward layered polymeric multicomposites," Science, 277:1232-1237.

Fore et al. (2007) "Pulsed-interleaved excitation FRET measurements on single duplex DNA molecules inside C-shaped nanoapertures," Nano Lett. 7(6):1749-1756.

Foster et al. (2006) "Friction force microscopy of alkylphosphonic acid and carboxylic acids adsorbed on the native oxide of aluminum," Langmuir, 22(22):9254-9259.

Gardner et al. (1995) "Systems for orthogonal self-assembly of electroactive monolayers on Au and ITO—an approach to molecular electronics," J. Am. Chem. Soc., 117(26):6927-6933.

Glatthar and Giese (2000) "A new photocleavable linker in solid-phase chemistry for ether cleavage," Org. Lett., 2(15):2315-2317.

Herrwerth et al. (2003) "Factors that determine the protein resistance of oligoether self-assembled monolayers—internal hydrophilicity, terminal hydrophilicity, and lateral packing density," J. Am. Chem. Soc., 125(31):9359-9366.

Hodneland and Mrksich (2000) "Biomolecular Surfaces that Release Ligands under Electrochemical Control," J. Am. Chem. Soc., 122(17):4235-4236.

Hofer et al. (2001) "Alkyl Phosphate Monolayers, Self-Assembled from Aqueous Solution onto Metal Oxide Surfaces," Langmuir,17(13):4014-4020.

Huang et al. (2002) "Biotin-Derivatized Poly(L-lysine))-g-Poly(ethylene glycol): A Novel Polymeric Interface for Bioaffinity Sensing" Langmuir, 18(1): 220-230.

Kambhampati et al. (2001) "Novel silicon dioxide sol-gel films for potential sensor applications: a surface plasmon resonance study," Langmuir, 17:1169-1175.

Kelley et al. (2003) "High-Performance OTFTs Using Surface-Modified Alumina Dielectrics," J. Phys. Chem. B, 107(24):5877-5881.

Libera et al. (2005) "Comparative X-ray standing wave analysis of metal-phosphonate multilayer films of dodecane and porphyrin molecular square," J. Phys. Chem. B 109(4):1441-1450.

Liu et al. (2004) "Biosensing based upon molecular confinement in metallic nanocavity arrays," Nanotechnology, 15:1368-1374.

Love et al. (2005) "Self-assembled monolayers of thiolates on metals as a form of nanotechnology," Chem. Rev. 105(4):1103-1169.

Messerschmidt and Schwartz (2001) Growth Mechanisms of Octadecylphosphonic Acid Self-Assembled Monolayers on Sapphire (Corundum): Evidence for a Quasi-equilibrium Triple Point, Langmuir, 17(2):462-467.

Michel et al. (2002) "A novel approach to produce biologically relevant chemical patterns at the nanometer scale: Selective molecular assembly patterning combined with colloidal lithography," Langmuir, 18(22):8580-8586.

Michel et al. (2002) "Selective molecular assembly patterning: A new approach to micro- and nanochemical patterning of surfaces for biological applications," Langmuir, 18(8):3281-3287.

Mutin et al. (2004) "Selective Surface Modification of $SiO_2$—$TiO_2$ Supports with Phosphonic Acids," Chemistry of Materials, 16(26):5670-5675.

Novotny et al. (1997) "Theory of Nanometric Optical Tweezers.," Phys. Rev. Letts. 79(4):645-648.

Osborn & Yager (1995) "Formation of planar solvent-free phospholipid bilayers by Langmuir-Blodgett transfer of monolayers to micromachined apertures in silicon," Langmuir, 11:8-12.

Pellerite et al. (2003) "Effects of Fluorination on Self-Assembled Monolayer Formation from Alkanephosphonic Acids on Aluminum: Kinetics and Structure," J. Phys. Chem. B, 107(42):11726-11736.

Raman et al. (2006) "Formation of self-assembled monolayers of alkylphosphonic acid on the native oxide surface of SS316L," Langmuir, 22(15):6469-6472.

Ramsier et al. (1988) "Adsorption of phosphorus-acids on alumina," Surface Science, 203(1-2):72-88.

Rodebaugh et al. (1997) "A new o-nitrobenzyl photocleavable linker for solid phase synthesis," Tetrahedron Lett., 38(44), 7653-7656.

Rossetti et al. (2005) "Interactions between titanium dioxide and phosphatidyl serine-containing liposomes: formation and patterning of supported phospholipid bilayers on the surface of a medically relevant material," Langmuir, 21(14):6443-6450.

Tosatti et al. (2002) "Self-Assembled Monolayers of Dodecyl and Hydroxy-dodecyl Phosphates on Both Smooth and Rough Titanium and Titanium Oxide Surfaces," Langmuir,18(9):3537-3548.

Voros et al. (2003) "Polymer Cushions to Analyze Genes and Proteins" BioWorld 2:16-17.

Xia and Whitesides (1996) "Shadowed sputtering of gold on V-shaped microtrenches etched in silicon and applications in microfabrication," Advanced Materials, 8(9):765-768.

Zoulalian et al. (2006) "Functionalization of titanium oxide surfaces by means of poly(alkyl-phosphonates)" J. Phys. Chem. B 110(51):25603-25605.

Zwahlen et al. (2002) "Orientation in Methyl- and Hydroxyl-Terminated Self-Assembled Alkanephosphate Monolayers on Titanium Oxide Surfaces Investigated with Soft X-ray Absorption," Langmuir, 18(10):3957-3962.

Cha et al. (2004) "Immobilization of oriented protein molecules on poly(ethylene glycol)-coated Si(111)," Proteomics, 4(7):1965-1976.

Ruiz-Taylor et al. (2001) "Monolayers of derivatized poly(L-lysine)-grafted poly(ethylene glycol) on metal oxides as a class of biomolecular interfaces," PNAS, 98(3)852-857.

Sofia et al. (1998) "Poly(ethylene oxide) grafted to silicon surfaces: grafting density and protein adsorption," Macromolecules, 31:5059-5070.

Yeo & Mrksich (2003) "Self-Assembled Monolayers That Transduce Enzymatic Activities to Electrical Signals," Angew. Chem. Int. Ed., 42:3121-3124.

Hong et al. (2003) "Self-Assembly of a Dendron through Multiple Ionic Interaction to Give Mesospacing between Reactive Amine Groups on the Surface", Langmuir, 19(6):2357-2365.

First Office Action dated Aug. 28, 2012 from related application CN 201110071662.4.

Eid et al. (2009) "Real-Time DNA Sequencing from Single Polymerase Molecules," Science, 323:133-138.

Foquet et al. (2008) "Improved fabrication of zero-mode waveguides for single-molecule detection," Journal of Applied Physics, 103:034301.

Korlach et al. (2008) "Selective aluminum passivation for targeted immobilization of single DNA polymerase molecules in zero-mode waveguide nanostructures," PNAS, 105(4):1176-1181.

M.J. Levene et al. (Jan. 31, 2003) "Zero-Mode Waveguides for Single-Molecule Analysis at High Concentrations." *Science*, 299: 682-686.

* cited by examiner

SELECTIVELY FUNCTIONALIZED ARRAYS

CROSS-REFERENCE TO RELATED APPLICATIONS

This application claims the benefit of U.S. Provisional Application No. 61/225,507, filed Jul. 14, 2009, the full disclosure of which is incorporated herein by reference in its entirety for all purposes.

STATEMENT REGARDING FEDERALLY SPONSORED RESEARCH

Not Applicable.

BACKGROUND OF THE INVENTION

There are a wide range of analytical operations that may benefit from the ability to analyze the reaction of individual molecules or a relatively small numbers of molecules. A number of approaches have been described for providing these sparsely populated reaction mixtures. For example, in the field of nucleic acid sequence determination, a number of researchers have proposed single molecule or low copy number approaches to obtaining sequence information in conjunction with the template dependent synthesis of nucleic acids by the action of polymerase enzymes.

The various different approaches to these sequencing technologies offer different methods of monitoring only one or a few synthesis reactions at a time. For example, in some cases, the reaction mixture is apportioned into droplets that include low levels of reactants. In other applications, certain reagents are immobilized onto bead or planar surfaces such that they may be monitored without interference from other reaction components in solution. In still another approach, optical confinement techniques have been used to ascertain signal information only from a relatively small number of reactions, e.g., a single molecule, within an optically confined area.

For arrays of optical confinements it can be desirable to have different characteristic properties on various different portions of the surfaces of the optical confinement structures. For example, different surface properties for portions of the surfaces within the observation regions and outside of the observation regions of the optical confinements. Notwithstanding the availability of the above-described techniques, there are instances where greater selectivity of reaction components for analysis would be desirable. The present invention meets these and a variety of needs.

BRIEF SUMMARY OF THE INVENTION

One aspect of the invention is method for selectively functionalizing a surface of a substrate having both silica-based portions and metal or metal oxide portions comprising; a) exposing a surface of a substrate having both silica-based portions and metal or metal oxide portions to an agent that preferentially binds to the metal or metal oxide portions to produce a passivated metal or metal oxide portions of the surface; b) exposing the surface of the substrate to a silica functionalizing agent that binds to both the silica-based portions and the metal or metal oxide portions of the surface; and c) exposing the surface of the substrate to a selective removal compound that preferentially removes the silica functionalizing agent from the passivated metal or metal oxide portions of the surface. In some embodiments the steps are carried out in the order a), b), c). In some embodiments the steps are carried out in the order b), c), a).

In some embodiments the agent that preferentially binds to the metal or metal oxide portions comprises phosphate or phosphonate functionality. In some embodiments the agent that preferentially binds to the metal or metal oxide portions comprises a polymer. In some embodiments the agent that preferentially binds to the metal or metal oxide portions comprises a polymer having poly(acrylate), poly(sulfonate), or both poly(acrylate) and poly(sulfonate) portions. In some embodiments the agent that preferentially binds to the metal or metal oxide portions comprises polyvinyl phosphonic acid (PVPA) or phosphorous containing polymeric materials, ALBRITECT CP-30, ALBRITECT CP-10, ALBRITECT CP-90, AQUARITE ESL, or AQUARITE EC4020.

In some embodiments the silica functionalizing agent comprises a silane coupling agent. In some embodiments the silane functionalizing agent comprises an aminosilane. In some embodiments the silane functionalizing agent comprises a silane comprising a biotin group. In some embodiments the silane functionalizing agent comprises a compound having the structure silane-polyethylene glycol-biotin. In some embodiments the silica functionalizing agent used for exposing the surface in step (b) comprises a mixture of silane functionalizing agents.

In some embodiments the selective removal compound comprises an acidic compound. In some embodiments the selective removal compound comprises a compound having a pKa of less than about 6. In some embodiments the selective removal compound comprises a polymer. In some embodiments the polymer comprises carboxylate, sulfonate, sulfate, phosphonate or phosphate functionality. In some embodiments the polymer comprises a homopolymer or copolymer of one or more of the monomers vinyl(acrylic acid), vinyl (sulfonic acid), vinyl(phosphonic acid), vinyl(styrenesulfonic acid), maleic acid, or salts thereof. In some embodiments the polymer comprises AQUARITE ESL (an acidic phosphonate containing polymer) or poly(vinylsulfonic acid) (PVSA).

In some embodiments the silica-based portions comprise optical confinement regions.

In some embodiments the substrate comprises an array of optical confinement regions wherein the silica-based portions comprise bases of apertures though a metal or metal oxide layer on a transparent silica-based substrate.

An aspect of the invention is method for selectively functionalizing a surface of a substrate having both silica-based portions and metal or metal oxide portions comprising; a) treating a surface of a substrate having both silica-based portions and metal or metal oxide portions with a compound comprising phosphate or phosphonate groups; b) treating the surface of the substrate with a silica functionalizing agent that binds to both the silica-based and metal or metal oxide portions of the surface; and c) treating the surface of the substrate with an acidic compound to remove silica functionalizing agent from the metal or metal oxide portions of the surface.

One aspect of the invention is a method for attaching a desired molecule to a silica-based portion of a surface of a substrate having both silica-based portions and metal or metal oxide portions comprising; a) exposing a surface of a substrate having both silica-based portions and metal or metal oxide portions to an agent that preferentially binds to the metal or metal oxide portions to produce passivated metal or metal oxide portions of the surface; b) exposing the surface of the substrate to a coupling agent that binds to both the silica-based portions and the metal or metal oxide portions of the surface; c) exposing the surface of the substrate to a selective removal compound that preferentially removes the coupling agent from the passivated metal or metal oxide portions of the surface; and d) attaching the desired molecule to the coupling agent bound to the silica-based portions of the surface.

In some embodiments step d) of attaching the desired molecule is carried out prior to step c) of exposing the surface of the substrate to a selective removal compound.

In some embodiments the coupling agent comprises a silane coupling agent. In some embodiments the silane coupling agent comprises an amino silane or a thiol-silane. In some embodiments the silane coupling agent comprises biotin. In some embodiments the silane coupling agent comprises a molecule having the structure silane-polyethylene glycol-biotin.

In some embodiments the attaching of the desired molecule to the to the coupling agent of step (d) comprises process wherein the coupling agent is reacted with an attaching agent, the attaching agent having a group which reacts with the coupling agent and a group for attaching the desired molecule. In some embodiments the attaching agent comprises biotin.

In some embodiments the coupling agent exposed to the surface in step (b) is mixed with a compound that reacts with the silica-based portions of the surface, but does not have coupling functionality.

In some embodiments the desired molecule comprises biotin and is attached to the silica portions of the surface using a protein having a high binding affinity for biotin. In some embodiments the desired molecule comprises an enzyme. In some embodiments the desired molecule comprises a polymerase enzyme.

In some embodiments the silica-based portions comprise optical confinement regions. In some embodiments the substrate comprises an array of optical confinement regions wherein the silica-based portions comprise bases of apertures though a metal or metal oxide layer on a transparent silica-based substrate. In some embodiments the metal or metal oxide portions comprise aluminum.

One aspect of the invention is a method for attaching a desired molecule to a silica-based portion of a surface of a substrate having both silica-based portions and metal or metal oxide portions comprising; a) treating a surface of a substrate having both silica-based portions and metal or metal oxide portions with a compound comprising phosphate of phosphonate groups; b) treating the surface of the substrate with a coupling agent that binds to both the silica-based and metal or metal oxide portions of the surface; c) treating the surface of the substrate with an acidic compound to remove coupling agent from the metal or metal oxide portions of the surface; and d) attaching the desired molecule to the coupling agent bound to the silica-based portions of the surface.

One aspect of the invention is an array of optical confinements having a surface with both a silica-based and a metal or metal-oxide portion that is prepared by the selective functionalization methods of the invention.

One aspect of the invention is an array of optical confinements having a surface with both a silica-based and a metal or metal-oxide portion, wherein the array has been treated with a biotin containing coupling agent and a passivating agent, wherein when a coupon having regions with the same type of silica as the silica-based portions and the same type of metal or metal-oxide as the metal or metal oxide portions of the array is treated in the same manner as the array, the coupon exhibits a fluorescence intensity bias of greater than 10 in a labeled neutravidin bead bias assay.

One aspect of the invention is an array of optical confinements having a surface with both a silica-based and a metal or metal-oxide portion, wherein the array has been treated with a biotin containing coupling agent and a passivating agent, wherein when a coupon having regions with the same type of silica as the silica-based portions and the same type of metal or metal-oxide as the metal or metal oxide portions of the array is treated in the same manner as the array, the coupon exhibits a fluorescence intensity bias of greater than 10 in a labeled template/polymerase complex bias assay.

One aspect of the invention is an apparatus for obtaining sequence information from a template nucleic acid comprising: a) a substrate comprising an array of zero-mode-waveguides wherein the zero-mode-waveguides comprise apertures through an upper metal layer disposed on top of a lower silica-based layer wherein the bias each zero-mode-waveguide capable of holding a single molecule of a polymerase enzyme, wherein the substrate is treated by a selective functionalization methods of the invention; b) a receptacle for keeping sequencing reagents in contact with the substrate; c) an optical system optically coupled to the substrate for delivering light to the zero-mode-waveguides and for measuring light from the zero mode waveguides over a period of time, wherein the measured light from the zero-mode-waveguide over a period of time can be used to obtain sequence information about the template DNA; and d) a computational system connected to the optical system for determining sequence information using the measured light over a period of time.

One aspect of the invention is an apparatus for obtaining sequence information from a template nucleic acid comprising: a) an array of zero-mode-waveguides wherein the zero-mode-waveguides comprise apertures through an upper metal layer disposed on top of a lower silica-based layer wherein when a coupon having regions with the same type of silica as the lower silica-based layer and the same type of metal as the upper metal layer is treated in the same manner as the array, the coupon exhibits a fluorescence intensity bias of greater than 10 in a labeled neutravidin bead bias assay; b) a receptacle for keeping sequencing reagents in contact with the substrate; c) an optical system optically coupled to the substrate for delivering light to the zero-mode-waveguides and for measuring light from the zero mode waveguides over a period of time, wherein the measured light from the zero-mode-waveguide over a period of time can be used to obtain sequence information about the template DNA; and d) a computational system connected to the optical system for determining sequence information using the measured light over a period of time.

BRIEF DESCRIPTION OF THE DRAWINGS

FIG. 7(a) illustrates a molecule of interest tethered to the bilayer. FIG. 7(b) illustrates a molecule of interest associated directly with the bilayer.

DETAILED DESCRIPTION OF THE INVENTION

I. General

Figure 1:
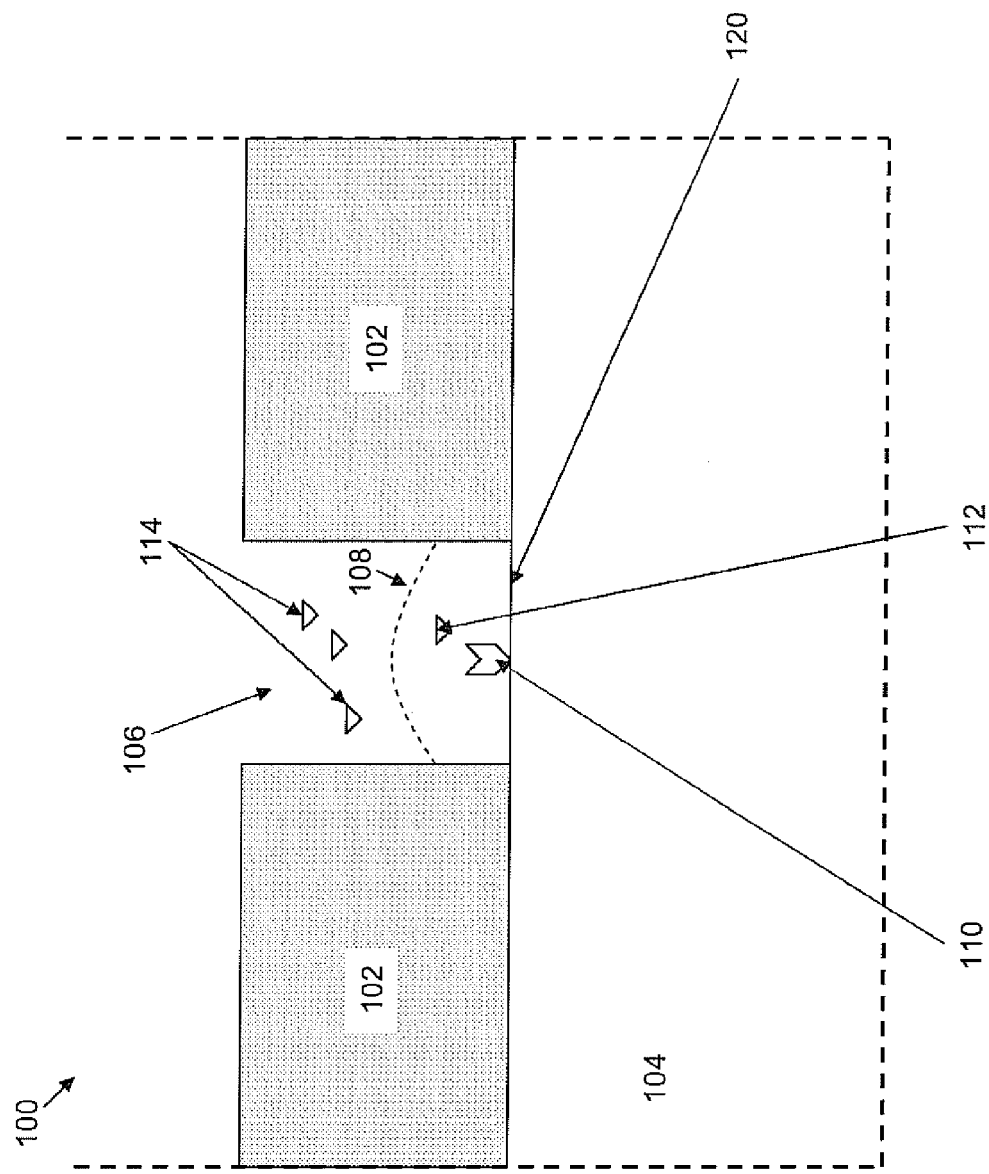
FIG. 1 shows a schematic illustration of a zero-mode-waveguide optical confinement.

The present invention is generally directed to methods and processes for providing desired molecules in preselected locations or areas on a substrate or within a set volume, and articles made from such methods or processes, and particularly, in desired low concentrations or as individual molecules, within an optical confinement. In particularly preferred aspects, the invention is directed to methods for localizing individual molecules within a particular space or volume, such that the spatial individuality of the molecule may be exploited, e.g., chemically, optically, electrically, or the like. The invention also provides the substrates, devices, receptacles and the like, e.g., the optical confinements, produced by these processes. While the processes of the invention may be broadly practical in providing individual molecules within any of a variety of given desired space or volume types, in particularly preferred aspects, the processes are used to selectively deposit or immobilize a desired molecule, such as an enzyme, within the optically accessible portion of an optical confinement, and particularly, a zero mode waveguide (ZMW).

The invention provides for a preferentially functionalized substrates in which, for example, a reflective or opaque region of a substrate surface is treated to have one set of surface characteristics, and a transparent portion of the surface is treated to have a different set of surface characteristics. In some aspects, an opaque or reflective region of the substrate is coated with a passivating compound, and a transparent region of the substrate surface has bound to it coupling agent to which a desired molecule may be preferentially bound. The methods of the invention provide for surfaces having either no coupling agent or very low levels of coupling agent bound to the reflective or opaque regions, while having sufficient coupling agent on the transparent regions for the substrates to be used, for example, for molecular analysis. In some cases, the methods of the invention can also be employed to functionalize the opaque or reflective portions, while passivating the transparent or silica based portions of the substrate.

We have found that a substrate having useful properties can be prepared a process including the steps of: (1) treating the substrate with a passivating compound that preferentially binds to the reflective or opaque surface regions, (2) treating the substrate with a coupling agent that reacts with the transparent surface regions, and (3) treating the substrate with a compound that preferentially removes the coupling agent from the reflective or opaque regions. We have found that by performing all three of these steps, surfaces having very little to no coupling agent on the reflective or opaque surface regions can be produced. The methods of the invention can be applied, for example, to a substrate comprising a lower layer made of a silica-based material such as fused silica and an upper metal cladding layer comprising a metal such as aluminum. The chemical differences of these surfaces can be utilized, for example, by incorporating a phosphorous containing selective passivating agent which reacts preferentially with the metal, e.g. aluminum, surface. The preferential removal of coupling agent from a metal, e.g. aluminum, surface can be accomplished using an acidic compound, such as a polymer comprising one or more of carboxylic acid, sulfonic acid, or phosphoric acid moieties. We have found that these compounds can selectively remove a coupling agent, such as a silane coupling agent from a passivated metal, e.g. aluminum, surface.

In general, optical confinements are used to provide electromagnetic radiation to or derive such radiation from only very small spaces or volumes. Such optical confinements may comprise structural confinements, e.g., wells, recesses, conduits, or the like, or they may comprise optical processes in conjunction with other components, to provide illumination to or derive emitted radiation from only very small volumes. Examples of such optical confinements include systems that utilize, e.g., total internal reflection (TIR) based optical systems whereby light is directed through a transparent portion of the substrate at an angle that yields total internal reflection within the substrate. Notwithstanding the TIR, some small fraction of the light will penetrate beyond the outer surface of the substrate and decay rapidly as a function of distance from the substrate surface, resulting in illumination of very small volumes at the surface. Similarly, ZMW structures may be employed that utilize a narrow core, e.g., from about 10 nm to about 200 nm, disposed through a cladding layer where the core is dimensioned such that the desired electromagnetic radiation is prevented from propagating through the core. As a result, the radiation will permeate the core only a very short distance from the opening of the core, and consequently illuminate only a very small volume within the core. A variety of other optical confinement techniques, including, e.g., field enhancement by sharp metal tips, nanotube confinement, thin slit confinement, near-field resonant energy transfer confinement, near field aperture confinement, diffraction limited optical confinement, and stimulated emission depletion confinement, are contemplated, as well as all other confinements described in pending U.S. Pat. Nos. 7,170,050, 7,056,661, and 6,917,726, each of which is incorporated herein by reference in its entirety for all purposes.

Zero mode waveguides (ZMWs) are generally characterized by the existence of a core surrounded by a cladding, where the core is dimensioned such that it precludes a substantial amount of electromagnetic radiation that is above a cut-off frequency from propagating through the core. As a result, when illuminated with light of a frequency below the cutoff frequency, the light will only penetrate a short distance into the core, effectively illuminating only a small fraction of the core's volume. In accordance with the present invention, the core comprises an empty or preferably fluid filled cavity surrounded by the cladding layer. This core then provides a zone or volume in which a chemical, biochemical, and/or biological reaction may take place that is characterized by having an extremely small volume, and in some cases sufficient to include only a single molecule or set of reacting molecules. ZMWs, their fabrication, structure, and use in analytical operations are described in detail in U.S. Pat. No. 6,917,726 and Levene, et al., Science 299(5607):609-764 (2003), the full disclosures of which are hereby incorporated herein by reference in their entirety for all purposes.

In the context of chemical or biochemical analyses within ZMWs as well as other optical confinements, it is clearly desirable to ensure that the reactions of interest are taking place within the optically interrogated portions of the confinement, at a minimum, and preferably such that only the reactions of a single molecule is occurring within an interrogated portion of an individual confinement. A number of methods may generally be used to provide individual molecules within the observation volume. A variety of these are described in co-pending U.S. patent application Ser. No. 11/240,662, filed Sep. 30, 2005, incorporated herein by reference in its entirety for all purposes, which describes, inter alfa, modified surfaces that are designed to immobilize individual molecules to the surface at a desired density, such that approximately one, two, three or some other select number of molecules would be expected to fall within a given observation volume. Typically, such methods utilize dilution techniques to provide relatively low densities of coupling groups on a surface, either through dilution of such groups on the surface or dilution of intermediate or final coupling groups that interact with the molecules of interest, or combinations of these.

In some cases, it may be further desirable that reactions of interest be reduced or even eliminated from other regions outside of the observation volume, e.g., on the overall substrate housing ZMWs, the cladding layer, etc., both inside and outside of the observation volume. In some cases, it is also desirable to prevent molecules of interest from binding to the portions of the cladding that may within the illumination region. In particular, reactions that are outside of the range of interrogation may, nonetheless, impact the reaction of interest or the monitoring of that reaction, by affecting reaction kinetics through depletion of reagents, increasing concentration of products, contributing to signal background noise levels, e.g., through the generation of products or consumption of reactants, that may interfere with the interrogated reaction or that provide excessive detectable background product levels that diffuse into and out of the interrogation volume of the waveguide. Accordingly, selective and preferential deposition and/or immobilization of the reaction components within the observation volume are particular advantages of the invention. These are generally practicable both as an alternative to and, in some cases, in addition to the low density deposition methods referenced above. In the context of the foregoing, molecules of interest may be described as being preferentially located in a particular region, or localized substantially in a given region. It will be appreciated that use of the term preferentially is meant to indicate that the molecule is localized in a given location at a concentration or surface density that exceeds that of other locations in which it is not preferentially localized. Thus preferential immobilization of a given molecule in a first region will mean that the molecule is present in such region at a higher density or concentration than in other regions. Density in such regions may be as much as 20% greater, 30% greater, 50% greater, 100% greater, or upwards of 200%, up to 1000% or more of the concentration or density in other regions, and in some cases 100 times greater, 1000 times greater or more. Similar meaning is generally applicable to indications that a given molecule is substantially only located in a given region.

In the case of, for example, ZMWs used for single molecule enzymatic analysis, it may be desirable to provide a single enzyme molecule within the illumination volume of a waveguide, and preferably upon the bottom or base surface of the waveguide. As noted above, it may therefore be further desirable to ensure that additional enzyme molecules are not present upon surfaces other than the bottom surface, e.g., the walls of the core and/or the surfaces of the cladding layer that are not part of the core, and the like.

A particularly valuable application of the substrates produced by the process of the invention is in processes termed "single molecule sequencing applications." By way of example, a complex of a template nucleic acid, a primer sequence and a polymerase enzyme may be monitored, on a single molecule basis, to observe incorporation of each additional nucleotide during template dependent synthesis of the nascent strand. By identifying each added base, one can identify the complementary base in the template, and thus read off the sequence information for that template. In the context of ZMWs, an individual polymerase/template/primer complex may be provided within the observation volume of the ZMW. As each of four labeled (e.g., fluorescent) nucleotides or nucleotide analogs is incorporated into the synthesizing strand, the prolonged presence of the label on such nucleotide or nucleotide analogs will be observable by an associated optical detection system. Such sequencing processes and detection systems are described in, e.g., Published U.S. Patent Application No. 2003/0044781 and Published U.S. Patent Application No. 2007/0036511, the full disclosures of which are incorporated herein by reference in their entirety for all purposes. Such single molecule sequencing applications are envisioned as being benefited by the methods described herein, through the selected immobilization of polymerases, templates or primers or complexes of any or all of these, preferentially within selected regions on a substrate, and/or substantially not on other portions of the substrate.

Although generally discussed in terms of localization of enzymes or other macromolecular groups, for purposes of the present invention, the molecule of interest may be any of a variety of different functional molecules for which one desires to provide spatial individuality or enhanced localization. Such groups include active molecules, such as catalytic molecules like enzymes, but also include molecules with more passive functionality, e.g., non catalytic groups, such as binding or coupling groups, hydrophobic or hydrophilic groups, structural enhancement groups, e.g., for adhesion promotion, activatable or deactivatable groups, or the like. Binding or coupling groups may include small molecule coupling groups or they may include macromolecular coupling groups, e.g., antibodies, antibody fragments, specific binding pairs, such as avidin/biotin, binding peptides, lectins, complementary nucleic acids, or any of a variety of other binding groups. Catalytically active molecules will typically include any catalytically active molecule for which one desires spatial individuality, e.g., to exploit in single molecule analyses, or the like.

In at least one aspect, the present invention is directed to providing enhanced isolation of discrete reaction and/or observation regions. This is, to provide chemical and/or environmental isolation for such regions. In some cases, this is accomplished by providing a barrier or zone between reaction and/or observation regions that substantially prevents the diffusion of one or more reactants and/or products from outside a particular reaction zone from entering and potentially interfering with the reaction taking place therein, or the observation of that reaction. In providing the requisite isolation, one may focus on one or both of: (1) providing sufficient separation/isolation between neighboring reaction/observation regions; and (2) eliminating any potentially interfering components from the spaces between such neighboring regions, e.g., clearing any reactants, products and/or enzymes from such spaces, and creating a type of "demilitarized zone" between observation regions. The creation of such a demilitarized zone is described, for example, in U.S. patent application Ser. No. 11/731,748, which is included herein in its entirety by reference.

In some aspects, the invention can be utilized to selectively functionalizing within optical confinement regions on a substrate. One such optical confinement is the zero-mode-waveguide (ZMW). The basic functional structure of a ZMW structure is schematically illustrated in FIG. 1. As shown, a ZMW structure 100 is provided that includes a cladding layer 102 deposited upon a transparent layer 104. An aperture or core 106 is disposed through the cladding layer to expose the transparent layer 104 below. The aperture 106 has a base 120 that comprises the top surface of the transparent layer 104. As shown in FIG. 1, the base 120 of the aperture 106 is at the same level as the planar surface of the transparent layer 104. In some cases, the base 120 of the aperture 106 is not at the same level, and can be above or below the planar surface of the transparent layer 104 outside of the aperture. For example, in some cases, the base of the aperture can be below the level of the surface of the transparent 104, extending into the transparent layer 104. The core is dimensioned to provide optical confinement by attenuating or preventing propagation of electromagnetic radiation that falls below a cut-off frequency through the core. Instead, the light only penetrates a short distance into the core, illuminating a relatively small volume, indicated as bounded by the dashed line 108. By providing reactants of interest within the observation volume, e.g., enzyme 110 and substrate 112, one can selectively observe their operation without interference from reactants, e.g., substrates 114 outside the observation volume, e.g., above line 108. It will be understood by those in the art the intensity will fall off in the core with a certain function, e.g. exponentially, and that line 108 does not necessarily represent a line above which no light penetrates, but can represent, for example, a line at which the light falls to a certain absolute or relative intensity level.

Figure 2:
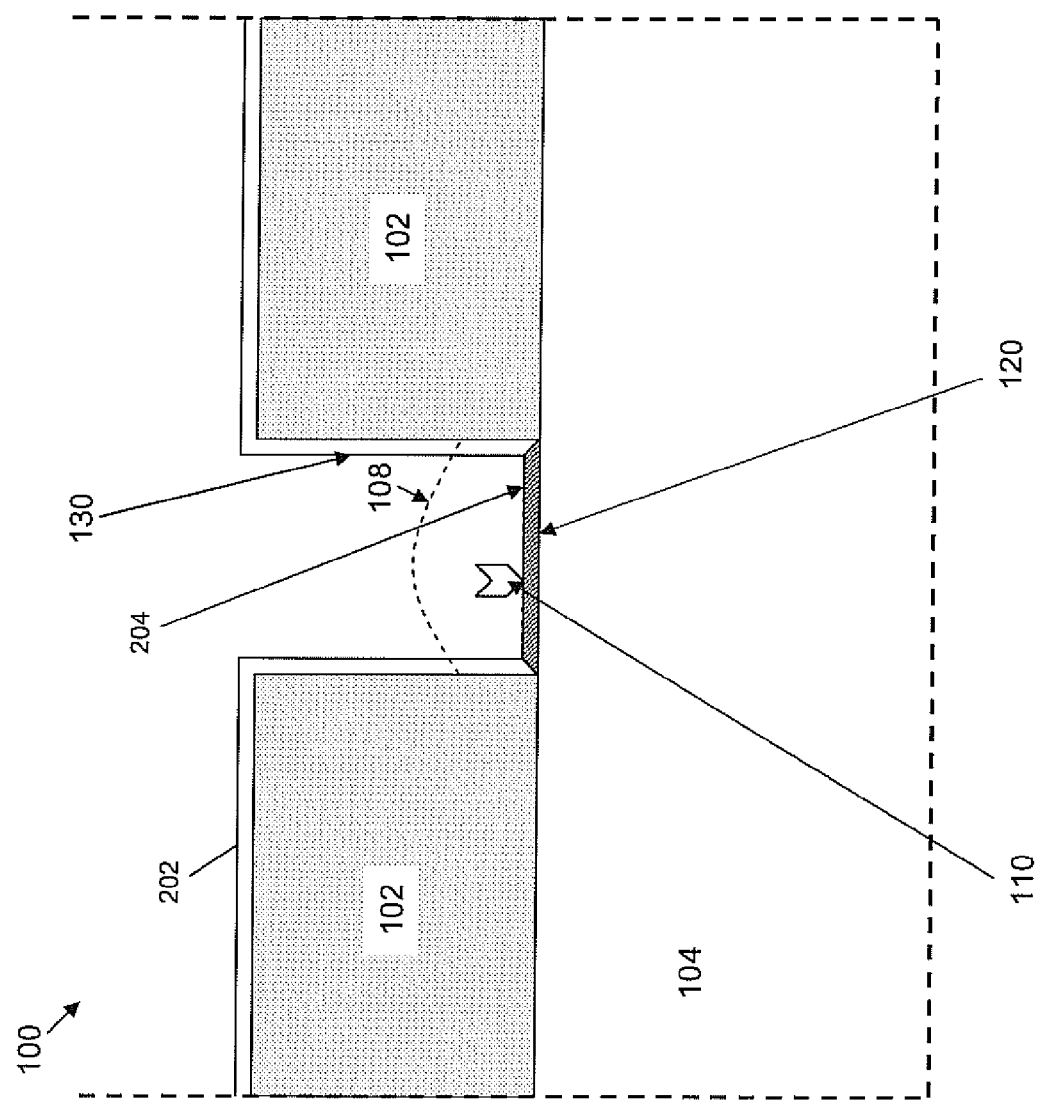
FIG. 2 shows an embodiment of a substrate of the invention having high bias.

FIG. 2 shows a ZMW having a surface modified as described in some aspects of the invention. In FIG. 2, the cladding 102 of the ZMW is selectively coated with a compound 202, for example a phosphate containing passivating compound. The exposed surface of the transparent layer 104 is functionalized, for example, with a silane coupling agent to produce a functionalized region 204 which comprises the base of the ZMW. The functionalized base of the ZMW will tend to be within the observation region of the ZMW, as illustrated by dashed line 108. The functionalized region can thus be accessible, for example, to illumination by light for the excitation of fluorescence within the sample. Where the functionalized region 204 comprises a coupling agent, the coupling agent can be used to attach a desired molecule (molecule of interest) 110 to the top surface 120 of the transparent layer 104. Methods of the invention allow for obtaining a ZMW having very little to no functionalizing groups, for example silane coupling agent, on the surfaces of the cladding, while efficiently functionalizing the base of the ZMW. These methods ensure that the desired molecules 110 are attached within the observation regions, and that desired molecules are not attached outside of the observation regions. In addition, the methods of the invention can also result in having very little to none of the passivating compounds on the transparent layer.

Figure 3:
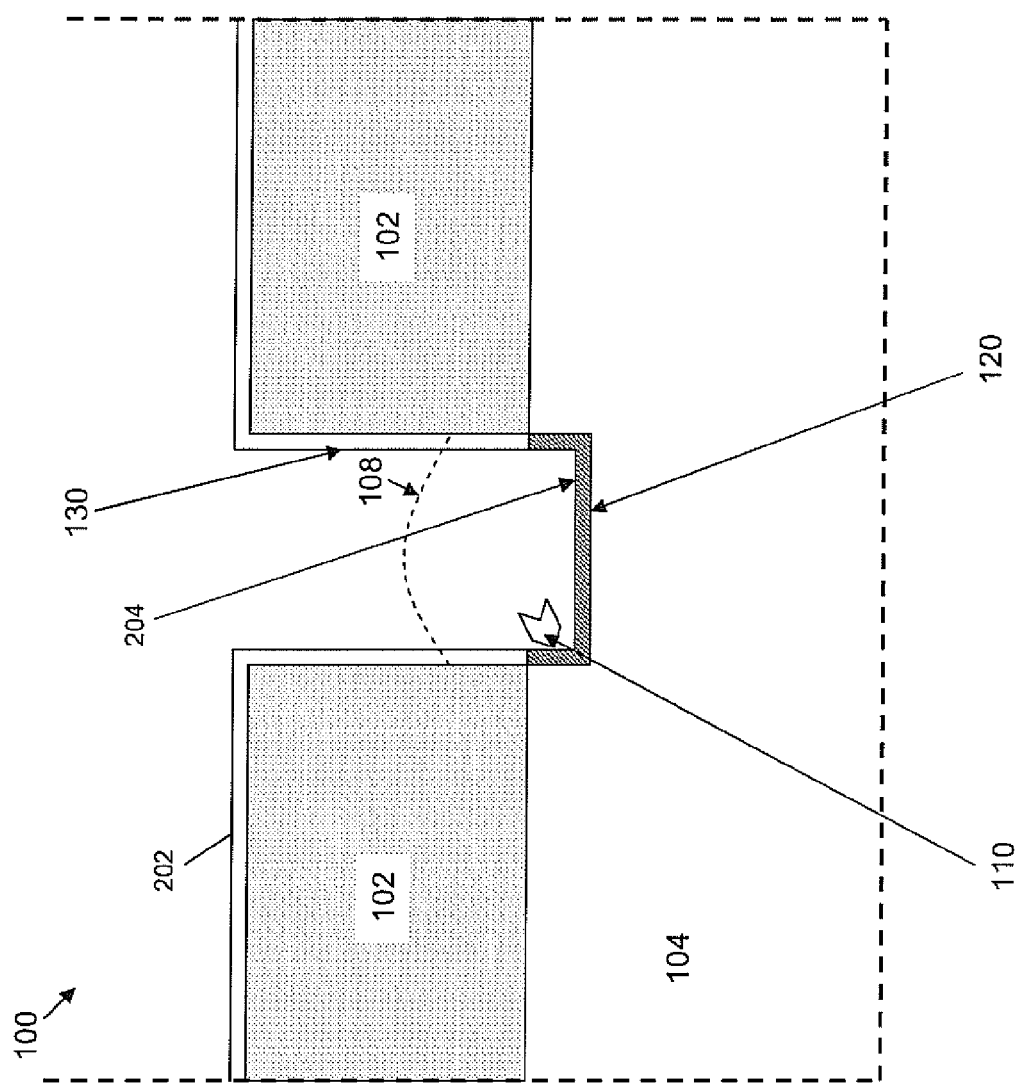
FIG. 3 shows an alternate embodiment of a substrate of the invention having high bias.

FIG. 3 shows a ZMW for which the aperture extends into the transparent layer having a surface modified as described in some aspects of the invention. In FIG. 3, the cladding 102 is selectively coated with a compound 202, for example a phosphate passivating agent. The exposed surface of the transparent layer 104 is functionalized, for example, with a silane coupling agent, to form a functionalized region 204. In this embodiment, the functionalized region 204 includes both the base, or floor, of the ZMW aperture, and also the sidewalls of the aperture where the aperture extends into the transparent region. The substrate is treated with a selective removal compound to selectively remove functionalized groups from the passivated surface of the cladding 202 to produce highly selectively coated surfaces. Where the transparent layer is functionalized with a coupling agent, a molecule of interest, such as an enzyme, can be attached. Here, since both the base of the aperture and the sidewalls of the aperture that extend into the transparent layer are functionalized, a molecule of interest could attach to either the base or that portion of the sidewall. Where a desired molecule 110 is attached to the wall of the aperture that extends into the transparent layer 104, the desired molecule will also be within the observation volume illustrated by dashed line 108. While illustrated for a ZMW array, the methods of the present invention can be used to selectively functionalize other substrates that have transparent or silica portions and reflective or metal portions such as the coupons described herein.

II. Methods

The methods of the invention are generally directed to the selective functionalization of substrates having both transparent and reflective or opaque regions. Such substrates can comprise, for example, an array of optical confinements or zero-mode-waveguide structures. In such arrays, it is often desirable to have specific functionality in different regions of the substrate. In some cases, it is desired that the level of specific functionality be high. One approach to obtaining high specific functionality is to utilize the different surface properties of the different types of materials that make up portions of the substrate surface. We have found that the methods described herein can provide for higher levels of specificity than other previously described methods.

For example, we have found that a surface having high specific functionality can be obtained with a method that comprises the three steps of: (a) exposing a surface of a substrate having both transparent, e.g. silica-based, portions and metal or metal oxide portions to an agent that preferentially binds to the metal or metal oxide portions to produce a passivated metal or metal oxide portions of the surface; (b) exposing the surface of the substrate to a transparent layer, e.g. silica, functionalizing agent that binds to both the transparent, e.g. silica-based, portions and the passivated metal or metal oxide portions of the surface; and (c) exposing the surface of the substrate to a selective removal compound that preferentially removes the transparent layer, e.g. silica, functionalizing agent from the passivated metal or metal oxide portions of the surface.

In some cases, the steps are carried out in the order described in which the selective removal agent is added after passivation and functionalization. The steps can also be carried out in the order b), c), then a) in which the passivation step is carried out after the selective removal step. We have found that the passivation step can be quite selective on its own, but that the step of functionalizing the silica or transparent portions of the surface typically results in some contamination of the metal or metal oxide portions of the surface. In some cases, the passivation and selective removal steps (steps a) and c)) can be combined and carried out at substantially the same time.

One preferred aspect of the invention provides a method for attaching a desired molecule selectively to a portion of a substrate. In one aspect the invention comprises a method for attaching a desired molecule to a silica-based portion of a surface of a substrate having both silica-based portions and metal or metal oxide portions comprising; a) exposing a surface of a substrate having both silica-based portions and metal or metal oxide portions to an agent that preferentially binds to the metal or metal oxide portions to produce passivated metal or metal oxide portions of the surface; b) exposing the surface of the substrate to a coupling agent that binds to both the silica-based portions and the passivated metal or metal oxide portions of the surface; c) exposing the surface of the substrate to a selective removal compound that preferentially removes the coupling agent from the passivated metal or metal oxide portions of the surface; and d) attaching the desired molecule to the coupling agent bound to the silica-based portions of the surface.

In some cases, we have found that it is desirable to carry out step d) prior to carrying out step c). A reason for carrying out step d) prior to step c) is provided were step c) of selective removal results in undesirable reactions with the coupling agent which lowers the yield of attaching step d). For example, we have found that where a thiol coupling agent is used, an acidic polymer selective removal compound can react with the thiol coupling agent and lower the yield of attaching the desired molecule, for example by maleimide coupling chemistry. In these cases, carrying out the attaching step d) first, can lead to a better yield of attachment of the molecule of interest.

While the treatment of surfaces made up of different materials to agents which react selectively with the different materials has been described, we have found that the use of a single selective treatment alone generally will not provide the specificity desired for applications such as producing arrays of optical confinements, for example, for observing the behavior of individual molecules. In particular, even where the second step described above of treating the transparent, e.g. silica-based, portions of the surface utilizes a highly selective functionalizing agent, and even where the metal or metal oxide portions are well passivated, there is generally still some amount of functionalizing agent bound to the passivated metal or metal oxide surface. We have found that the desired level of selective functionalization can be obtained by employing a selective removal compound that selectively removes functionalizing agent from the passivated metal or metal oxide surface, while removing little or no functionalizing agent from the transparent, e.g. silica portions.

Generally, the substrates comprise an opaque or reflective surface portion and a transparent surface portion, which may be silica based. It is not always required that the substrate have a transparent portion. For example, the substrate may have a silica-based portion that is not transparent, such as, for example, silicon, and a reflective surface, for example, a metal surface.

Figure 4:
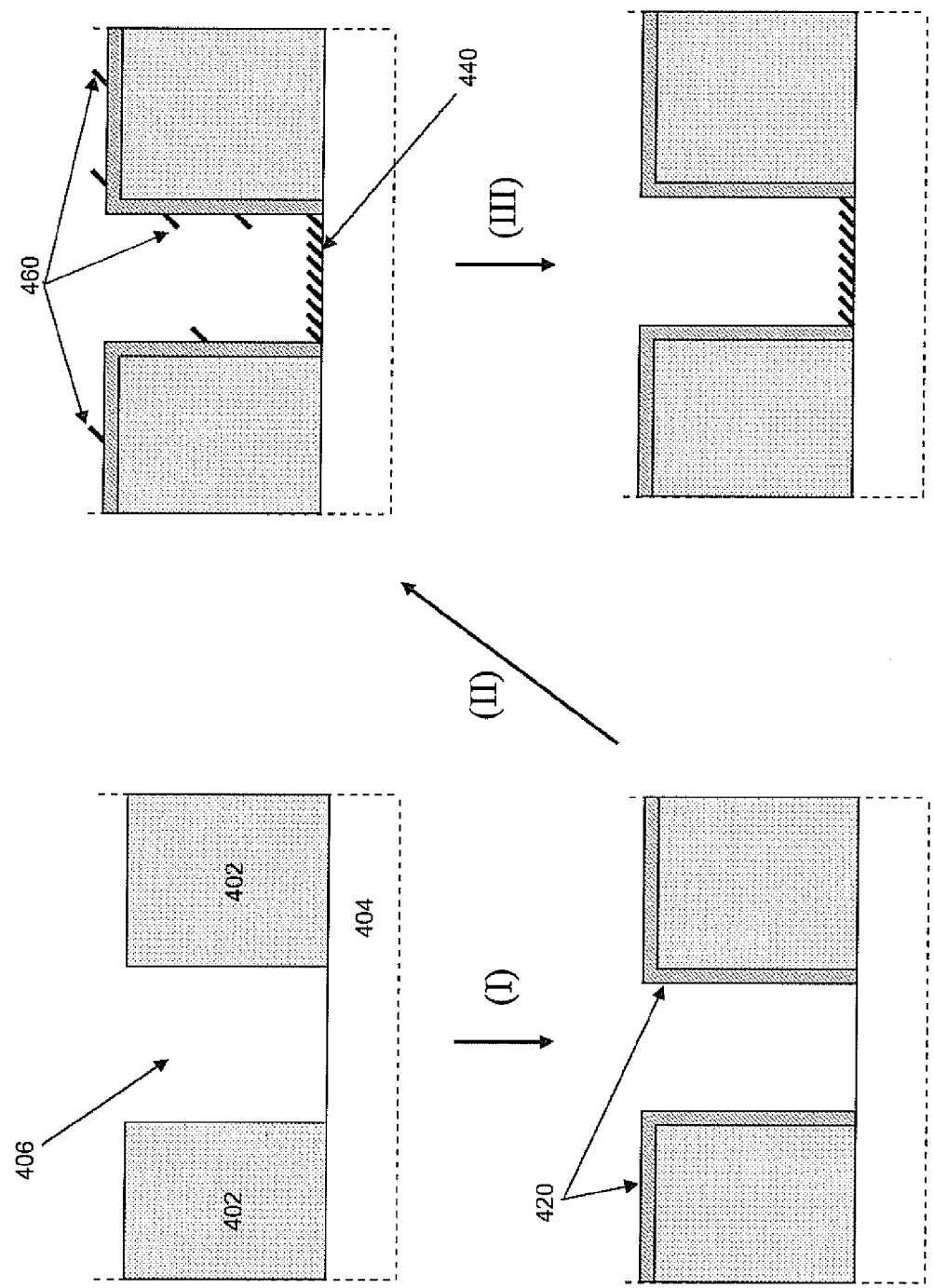
FIG. 4 illustrates an embodiment of a method of the invention for producing a substrate having a functionalized transparent or silica-based surface with high bias.

An embodiment of a method of the invention is shown schematically in FIG. 4. An optical confinement comprising an aperture 406 through a metal cladding layer 402, such as aluminum, to a transparent layer 404 is treated in step (I) with a selective passivating agent such as a phosphonate containing polymer. The selective passivating agent produces a passivation coating 420 selectively over the metal cladding layer. Very little to no selective passivating agent coats onto the transparent layer. In step (II) the substrate is treated with a transparent layer surface functionalizing agent such as a silane coupling agent. The functionalizing agent forms a coating 440 on the exposed transparent layer surface. While the functionalizing agent may be somewhat selective, unwanted functionalizing agent 460 can become deposited onto the metal cladding layer. In step (III), a selective removal agent is used to selectively remove functionalizing agent from the metal cladding layer, while leaving the functionalizing agent on the transparent layer. This process produces a functionalized transparent layer surface having high bias.

Figure 5:
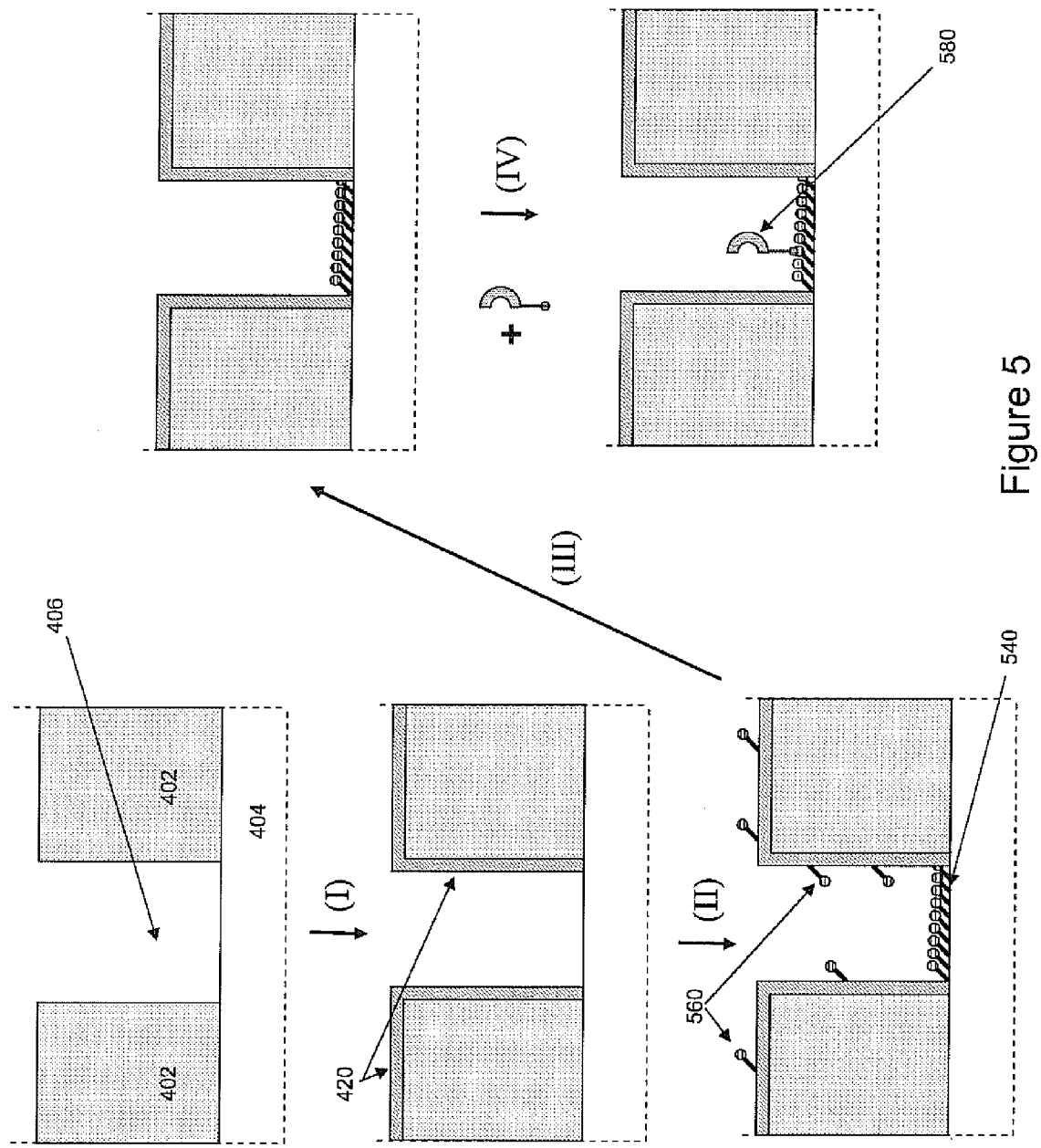
FIG. 5 illustrates an embodiment of a method of the invention for producing a substrate having coupling agent selectively bound to a transparent silica surface, and coupling of a molecule of interest to such surface.

Another embodiment of a method of the invention is shown schematically in FIG. 5. An optical confinement comprising an aperture 406 through a metal cladding layer 402, such as aluminum, to a transparent layer 404 is treated in step (I) with a selective passivating agent such as a phosphonate containing polymer. The selective passivating agent produces a passivation coating 420 selectively over the metal cladding layer. Very little to no selective passivating agent coats onto the transparent layer. In step (II) the substrate is treated with a coupling agent that binds to the exposed transparent layer surface. The coupling agent forms a coating 540 on the exposed transparent layer surface. While the coupling agent may be somewhat selective, unwanted coupling agent 560 can become deposited onto the metal cladding layer. In step (III), a selective removal agent is used to selectively remove coupling agent from the metal cladding layer, while leaving the coupling agent on the transparent layer. In step (IV), a molecule of interest having functionality that can bind to the coupling agent is added such that the molecule of interest becomes attached to the coupling agent selectively bound to the transparent layer surface. Since little or no coupling agent is present on the metal cladding layer due to the treatment with the selective removal agent, the molecule of interest is bound to the transparent layer surface with high bias. In some cases, the molecules of interest are added at a concentration such that a significant portion of the optical confinements have only one molecule of interest present.

Figure 6:
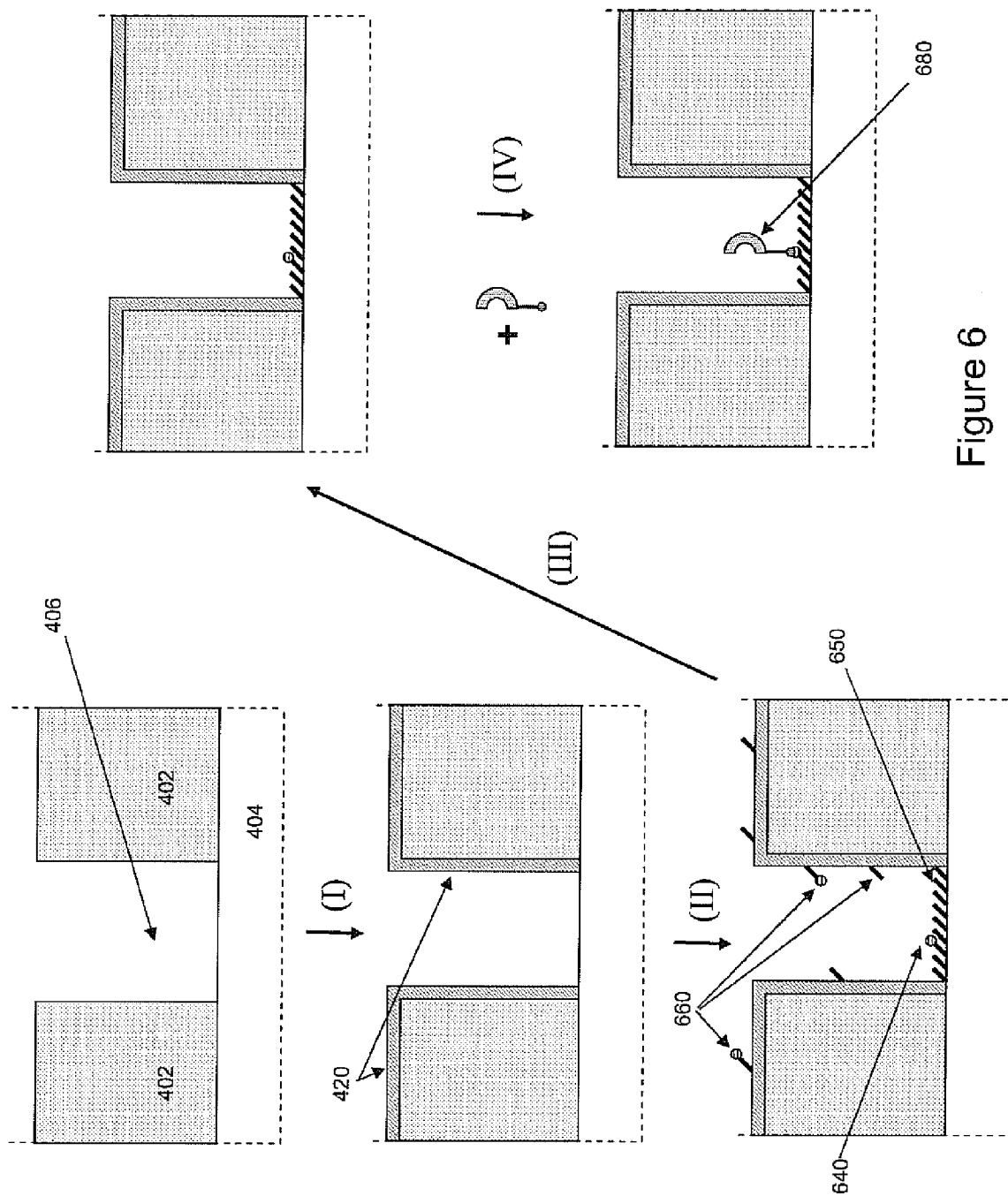
FIG. 6 illustrates an embodiment of a method of the invention for producing a substrate having a mixture of functionalizing agent including coupling agent selectively bound to a transparent silica surface, and coupling of a molecule of interest to such surface.

Yet another embodiment of a method of the invention is shown schematically in FIG. 6. An optical confinement comprising an aperture 406 through a metal cladding layer 402, such as aluminum, to a transparent layer 404 is treated in step (I) with a selective passivating agent such as a phosphonate containing polymer. The selective passivating agent produces a passivation coating 420 selectively over the metal cladding layer. Very little to no selective passivating agent coats onto the transparent layer. In step (II) the substrate is treated with a mixture of a coupling agent and a non-coupling functionalizing agent that binds to the exposed transparent layer surface. The coupling/functionalizing agent mix forms a coating on the exposed transparent layer surface that has both coupling agent 640 and non-coupling functionalizing agent 650. The coupling agent can be provided at low concentration in the mixed functionalizing agent such that a low density of coupling agents is disposed on the transparent layer surface. While the functionalizing agent mixture may be somewhat selective, unwanted coupling agent 660 can become deposited onto the metal cladding layer. In step (III), a selective removal agent is used to selectively remove functionalizing agent from the metal cladding layer, while leaving the functionalizing agents on the transparent layer. In step (IV), a molecule of interest having functionality that can bind to the coupling agent is added such that the molecule of interest becomes attached to the coupling agent selectively bound to the transparent layer surface. Since little or no coupling agent is present on the metal cladding layer due to the treatment with the selective removal agent, the molecule of interest is bound to the transparent layer surface with high bias. In some cases, the molecules of interest are added at a concentration such that a significant portion of the optical confinements have only one molecule of interest present.

In some cases, the processes of the invention up to the functionalization of the transparent or silane portions of the substrate will be carried out, and the substrate will be stored prior to carrying out the final treatment with the selective removal agent. For example, the sample can be stored for 2, 3, 4, 5, 6, or 7 days, or 2, 3, 4, 6, 8, or more weeks prior to treatment with the selective removal agent. Holding the sample before performing treating with the selective removal agent can be useful in cases, which we have observed wherein the surface is more stable prior to treatment with the selective removal agent than it is after such treatment.

Another method for obtaining a selectively functionalized surface, which is sometimes referred to as an MPP process comprises first functionalizing the transparent or silica based surface with a functionalizing agent such as a thiol functionalized silane, second, conjugating a coupling group or selective binding group such as biotin to the surface, for example using a Biotin-PEG-maleimide group, (where the Biotin-PEG-maleimide group is optionally diluted with a non-coupling surface reactive group or surface passivating group such as PEG-maleimide at a ratio of from about 10:1 to about 1:1,000,000, about 1:100 to about 1:100,000, or about 1:10,000 to about 1:1,000,000, third, treating the surface with a phosphonate passivating group such as PVPA, and fourth, treating the surface with an acidic phosphonate containing polymer such as AQUARITE ESL. In some embodiments the third and fourth steps are carried out simultaneously.

While in some cases the invention can involve masking specific portions of the surface to produce selectively functionalized regions, it is one aspect of the invention that the surface comprising the transparent or silica based portions and reflective or opaque portions are simultaneously treated with the reagents described herein, thus providing selective functionalization of the different regions of the surface without the use of masking the different portions.

A. Substrate

The substrate of the invention has a surface comprising two or more regions comprising different materials. The surface of the substrate may comprise, for example, regions of a transparent material and regions of an opaque or reflective material. In some cases, the surface comprises a silica-based material and a metal or metal oxide based material. The substrate can comprise a transparent layer which has disposed upon its surfaces regions of opaque or reflective materials. In addition, the substrate can comprise a silica-based material which has disposed upon its surface metal or metal oxide regions. The substrate can comprise an array of optical confinements or zero-mode-waveguides as described in U.S. Pat. No. 7,170,050 or 7,302,146 which are incorporated by reference herein in their entirety. The substrates generally comprise at least one surface on which a pattern of optical confinements is present, where the surface may be smooth or substantially planar, or have irregularities, such as depressions or elevations. The surface on which the pattern of targets is presented may be modified with one or more different layers of compounds that serve to modulate the properties of the surface in a desirable manner.

The substrates of the invention are generally rigid, and often planar, but need not be either. Where the substrate comprises an array of optical confinements, the substrate will generally be of a size and shape that can interface with optical instrumentation to allow for the illumination and for the measurement of light from the optical confinements. Typically, the substrate will also be configured to be held in contact with liquid media, for instance containing reagents and substrates and/or labeled components for optical measurements.

Where the substrates comprise arrays of optical confinements, the arrays may comprise a single row or a plurality of rows of optical confinement on the surface of a substrate, where when a plurality of lanes are present, the number of lanes will usually be at least 2, more commonly more than 10, and more commonly more than 100. The subject array of optical confinements may align horizontally or diagonally long the x-axis or the y-axis of the substrate. The individual confinements can be arrayed in any format across or over the surface of the substrate, such as in rows and columns so as to form a grid, or to form a circular, elliptical, oval, conical, rectangular, triangular, or polyhedral pattern. To minimize the nearest-neighbor distance between adjacent optical confinements, a hexagonal array is sometimes preferred.

The array of optical confinements may be incorporated into a structure that provides for ease of analysis, high throughput, or other advantages, such as in a microtiter plate and the like. Such setup is also referred to herein as an "array of arrays." For example, the subject arrays can be incorporated into another array such as microtiter plate wherein each micro well of the plate contains a subject array of optical confinements.

In accordance with the invention, arrays of confinements, e.g., zero mode waveguides, are provided in arrays of more than 100, more than 1000, more than 10,000, more that 100, 000, or more than 1,000,000 separate waveguides on a single substrate. In addition, the waveguide arrays typically comprise a relatively high density of waveguides on the surface of the substrate. Such high density typically includes waveguides present at a density of greater than 10 zero mode waveguides per $mm^2$, preferably, greater than 100 waveguides per $mm^2$ of substrate surface area, and more preferably, greater than 500 or even 1000 waveguides per $mm^2$ and in many cases up to or greater than 100,000 waveguides per mm $mm^2$. Although in many cases, the waveguides in the array are spaced in a regular pattern, e.g., in 2, 5, 10, 25, 50 or 100 or more rows and/or columns of regularly spaced waveguides in a given array, in certain preferred cases, there are advantages to providing the organization of waveguides in an array deviating from a standard row and/or column format. In preferred aspects, the substrates include zero mode waveguides as the optical confinements to define the discrete reaction regions on the substrate.

The optical confinements can be zero-mode-waveguides. Zero mode waveguides have been described in, e.g., U.S. Pat. No. 6,917,726, the full disclosure of which is incorporated herein by reference in its entirety for all purposes. Generally, such waveguides comprise a core disposed through a cladding layer, which in the case of applications to reactions, comprises an aperture disposed through the cladding layer that can receive the reactants to be monitored. Typically, the aperture has at least one cross-sectional dimension, e.g., diameter, which is sufficiently small that light entering the waveguide is prevented in some measure from propagating through the core, effectively resulting in a very small portion of the core and its contents being illuminated, and/or emitting optical signals that exit the core. In the case of optical signals (and excitation radiation), the waveguide cores will typically be between about 1 nm and about 300 nm, between about 10 and about 200 nm, or between about 50 and about 150 nm in diameter where light in the visible range is used.

The overall size of the array can generally range from a few nanometers to a few millimeters in thickness, and from a few millimeters to 50 centimeters in width and/or length. Arrays may have an overall size of about few hundred microns to a few millimeters in thickness and may have any width or length depending on the number of optical confinements desired.

The spacing between the individual confinements can be adjusted to support the particular application in which the subject array is to be employed. For instance, if the intended application requires a dark-field illumination of the array without or with a low level of diffractive scattering of incident wavelength from the optical confinements, then the individual confinements may be placed close to each other relative to the incident wavelength.

The individual confinement in the array can provide an effective observation volume less than about 1000 zeptoliters, less than about 900, less than about 200, less than about 80, less than about 10 zeptoliters. Where desired, an effective observation volume less than 1 zeptoliter can be provided. In a preferred aspect, the individual confinement yields an effective observation volume that permits resolution of individual molecules, such as enzymes, present at or near a physiologically relevant concentration. The physiologically relevant concentrations for many biochemical reactions range from micro-molar to millimolar because most of the enzymes have their Michaelis constants in these ranges. Accordingly, preferred array of optical confinements has an effective observation volume for detecting individual molecules present at a concentration higher than about 1 micromolar ($\mu M$), or more preferably higher than 50 $\mu M$, or even higher than 100 $\mu M$.

As zero-mode-waveguide can provide an optical guide in which the majority of incident radiation is attenuated, preferably more than 80%, more preferably more than 90%, even more preferably more than 99% of the incident radiation is attenuated. As such high level of attenuation, no significant propagating modes of electromagnetic radiation exist in the guide. Consequently, the rapid decay of incident electromagnetic radiation at the entrance of such guide provides an extremely small observation volume effective to detect single-molecules, even when they are present at a concentration as high as in the micromolar range.

The zero-mode-waveguide of the present invention typically comprises a cladding surrounding a core (i.e., partially or fully), wherein the cladding is configured to preclude propagation of electromagnetic energy of a wavelength higher than the cutoff wavelength longitudinally through the core of the zero-mode waveguide. The cladding is typically made of materials that prevent any significant penetration of the electric and the magnetic fields of an electromagnetic radiation that is opaque and/or reflective materials. Suitable materials for fabricating the cladding include but are not limited to metals, metal oxides, alloys, and semi-conducting materials, and any combination thereof.

The internal cavity (i.e., the core) surrounded by the cladding may adopt a convenient size, shape or volume so long as propagating modes of electromagnetic radiation in the guide is effectively prevented. The core typically has a lateral dimension less than the cutoff wavelength ($\lambda_c$). For a circular guide of diameter d and having a clad of perfect conductor, $\lambda_C$ is approximately 1.7 times d. The cross sectional area of the core may be circular, elliptical, oval, conical, rectangular, triangular, polyhedral, or in any other shape. Although uniform cross sectional area is generally preferred, the cross sectional area may vary at any given depth of the guide if desired.

In some embodiments, the core is non-cylindrical. In one aspect of this embodiment, a non-cylindrical core comprises an opening on the upper surface and a base at the bottom surface that is entirely enclosed by the cladding, wherein the opening is narrower in lateral dimension than the base. This configuration significantly restricts the diffusion of reactants, and hence increases the average residence time in the observation volume. Such configuration can be useful, for example, for measuring the association rate constant (on-rate) of a chemical reaction. In another aspect, the core comprises an opening that is wider in lateral dimension than the base. Such configuration allows easier access to large molecules that impose a steric or entropic hindrance to entering the structure if the open end of the zero mode waveguide was as small as the base needed to be for optical performance reasons. Examples include the accessibility for long strand polyelectrolytes such as DNA molecules that are subject to entropic forces opposing entry into small openings.

The surfaces of the substrate are modified according to the methods described herein. The surface modifications are generally carried out by laboratory and manufacturing techniques that would be known to those of skill in the art. In some cases, the compounds used for surface modification and surface functionalization are brought into contact with the surface in liquid form. For example, the surfaces are treated with or exposed to a solution of the surface modification compound. In other cases, the compounds are brought into contact with the surface in gaseous form. In general, the whole surface of the substrate is exposed to or treated with the compounds or functionalizing agents. In other cases, regions of the surface can be masked from exposure to one or more of the compounds or functionalizing agents.

B. Silica-Based Layer/Transparent Layer

The substrate generally comprises a silica-based and/or a transparent layer. The term "transparent", as used herein, refers to a layer will at least partially transmit electromagnetic energy or light of the wavelength appropriate for the use of the substrate. Where the substrate comprises an array of optical confinements, the wavelength is generally from the infrared to the ultraviolet. In many cases, for example in using fluorescent dyes, it is desirable that the substrate transmit visible light, for example, between 400 nm and 800 nm. The optically transparent layer may generally comprise any of a number of transparent solid materials, depending upon other components of the substrate. Such materials include inorganic materials, such as glass, quartz, fused silica, and the like. In some preferred embodiments, fused silica comprises the transparent layer. The transparent substrate can comprise an oxide material such as indium-tin oxide (ITO). In some cases, a transparent material which can be processed using semiconductor processing techniques, such as fused silica is preferred. Alternatively, such materials may include organic materials, such as polymeric substrates such as polystyrene, polypropylene, polyethylene, polymethylmethacrylate (PMMA), and the like. Polymeric materials having low levels of autofluorescence, such PMMA can be particularly useful in fluorescent or fluorogenic reactions.

In some embodiments, the substrate comprises a silica-based material. The silica-based material can be transparent or opaque. Suitable silica-based materials include glass, semiconductors (e.g., silicate, silicon, silicates, silicon nitride, silicon dioxide), quartz, fused silica, In some embodiments, the substrate comprises a semiconductor material that is not generally transparent. Suitable semiconductor materials include doped silicon, germanium, or gallium arsenide.

In some embodiments the transparent and/or silica based material comprises a structural component of the substrate. For example, where the substrate comprises an array of optical confinements, the array can comprise a transparent layer on which an opaque or reflective cladding layer is deposited. In such cases, it is generally desired that the transparent layer be relatively rigid, and of a thickness which will allow for handling without significant distortion or breakage. The thickness of the transparent layer will generally be 10 microns to a millimeter in thickness.

C. Opaque/Reflective Layer

The substrates of the invention in some embodiments comprise an opaque and/or a reflective layer. The opaque or reflective layer can be disposed upon the upper surface of a transparent lower layer. By patterning the opaque or reflective layer on the transparent lower layer, a plurality of optical confinements can be produced. In some cases the substrate comprises a single opaque or reflective layer. In some cases, the substrate comprises multiple opaque or reflective layers, which can comprise the same or different materials.

Where the substrate comprises an array of optical confinements, the opaque and/or reflective layer can also be referred to as the cladding. The cladding is typically made of materials that prevent any significant penetration of the electric and the magnetic fields of an electromagnetic radiation in the wavelength range of interest, e.g. opaque and/or reflective materials. Suitable materials for fabricating the opaque and/or reflective materials include but are not limited to metals, metal oxides, alloys, and semi-conducting materials, and any combination thereof. As used herein, the term metal includes alloys comprising a metal. Alloys generally include any of the numerous substances having metallic properties but comprising two or more elements of which at least one is a metal. Alloys may vary in the content or the amount of the respective elements-whether metallic or non metallic. Preferred alloys generally improve some desirable characteristics of the material over a pure elemental material. Characteristics that can be improved through the use of mixtures of materials include, chemical resistance, thermal conductivity, electrical conductivity, reflectivity, grain size, coefficient of thermal expansion, brittleness, temperature tolerance, conductivity, and/or reduce grain size of the cladding.

In some embodiments aluminum or an aluminum alloy comprises the metal in the zero-mode-waveguide. Non-limiting examples of materials suitable to alloy with aluminum are antimony, arsenic, beryllium, bismuth, boron, cadmium, calcium, carbon, cerium, chromium, cobalt, copper, gallium, hydrogen, indium, iron, lead, lithium, magnesium, manganese, mercury, molybdenum, nickel, niobium, phosphorous, silicon, vanadium, zinc, titanium, or combinations thereof. By way of example of how the introduction of another element could beneficially impact the ZMW performance, the introduction of boron to aluminum is known in the art of metallurgy to increase the conductivity of aluminum. Some embodiments include an alloy of aluminum that is more than 0.0001% of a dopant. Some embodiments include an alloy of aluminum that is more than 0.005% of a dopant. Some embodiments embodiment includes an alloy of aluminum that is more than 0.1% of a dopant.

Semi-conducting materials suitable for the opaque and/or reflective layer are generally opaque, and they include doped or undoped silicon, germanium, silicates, silicon nitride, silicon dioxide, gallium phosphide, gallium arsenide, metal oxides or any combinations thereof.

In many cases, the surfaces of metals will comprise metal-oxides. For example, when aluminum is exposed to air, the exposed surfaces will generally have a surface layer of aluminum oxide. Some aspects of the invention involve performing reactions on the surfaces of metals. When describing such reactions herein, it is to be understood that where the reaction with a metal at the surface of a metal is described, this reaction may be a reaction with, for example, a surface metal oxide or surface metal hydroxide. Alternatively, where a reaction may be described as occurring with a metal oxide such as an aluminum oxide, it is to be understood that in the context of the invention such a reaction can be carried out on the surface of a metal layer.

D. Selective Coating or Selective Passivation of the Opaque or Reflective Layer

Some aspects of the invention include the selective passivation of an opaque or reflective layer. Passivation of a surface generally means treating a surface to change the properties of the surface. In some cases, passivation can involve preventing the surface from participating in a chemical reaction that the surface would have if not passivated. For example, passivation can involve minimizing the surfaces interactions with the environment (e.g., minimizing or eliminating nonspecific binding to the surfaces). In particular, passivation can involve minimizing the binding of biomolecules or other reagents used in carrying out a reaction with biomolecules, such as proteins, nucleic acids, or nucleotides. In some cases, passivation can be minimizing a surface's tendency to undergo corrosion. In the context of the arrays of optical confinement described herein, it can be desirable that the opaque or passivation layer passivated with respect to the adsorption or binding of compounds in a solution which is observed with the optical confinement. For example, it can be undesirable for the silica or transparent layer functionalization agents or the molecules of interest to be bound to the surface of the opaque or reflective layer.

Passivation can, in some cases, be accomplished by coating the opaque or reflective surface with a passivating compound. In some cases, the passivating compound can be bound covalently to the opaque or reflective surface. In some cases, the passivating compound can be deposited onto the opaque or reflective surface without the formation of a covalent bond, being held in place, for example by van der Waals, hydrogen bonding, or dipolar forces In one aspect of the invention, the surface is treated with a passivating compound that selectively reacts with, and deposits onto the opaque or reflective surface, while having little or no deposition onto silica-based, or transparent surfaces.

Thus, selective coating of a given compound to an opaque or reflective layer as opposed to a silica-based or transparent layer means that the compound is present on the surface of an opaque or reflective layer such as a metal or metal oxide layer at a higher density or concentration than in other regions. Density in such regions may be as much as 20% greater, 30% greater, 50% greater, 100% greater, or upwards of 200%, up to 1000% or more than the concentration or density on the surface of a silica-based or transparent layer, and in some cases 100 times greater, 1000 times greater or more.

In some cases, the opaque or reflective layer comprises a metal or metal oxide surface such as aluminum or aluminum oxide surfaces, which tend to be positively charged in aqueous solution, and which can be passivated using a negatively charged passivating agent that binds to the metal or metal oxide surface.

Preferred passivation or coating compounds of the invention contain phosphorous. These compounds will generally comprise P=O and/or P—OH functionality. In particular, compounds comprising phosphate or phosphonate groups can be used. Such phosphate or phosphonate compounds can selectively react with metal or metal oxide surfaces such as aluminum or aluminum oxide, while having low reactivity to other surfaces, for example silica surfaces. In addition, in some cases, these compounds will form strong bonds to a metal or metal oxide surface such as the surface of aluminum to provide robust passivation to the metal surface. Preferred passivation or coating compounds include phosphorous containing polymeric materials. Suitable phosphorous containing polymeric materials include homopolymers and copolymers of poly(vinylphosphonic acid), ALBRITECT CP-30, ALBRITECT CP-10, ALBRITECT CP-90, AQUARITE ESL, and AQUARITE EC4020. ALBRITECT and AQUARITE compounds are commercially available from Rhodia, Inc. Phosphate or phosphonic acid moieties can bind strongly to metal oxides (e.g., aluminum oxide, titanium oxide, zirconium oxide, tantalum oxide, niobium oxide, iron oxide, and tin oxide) but do not generally bind strongly to silicon oxide. Thus, compounds that comprise at least one phosphate group (—OP(O)(OH)$_2$, whether protonated, partially or completely deprotonated, and/or partially or completely neutralized) or phosphonic acid group (—P(O)(OH)$_2$, whether protonated, partially or completely deprotonated, and/or partially or completely neutralized) can be used to selectively modify the aluminum layers having aluminum oxide surfaces of a ZMW or similar hybrid substrate.

For example, a metal oxide surface can be modified with an alkyl phosphate or an alkyl phosphonate. The terms phosphonic acid and phosphonate are alternatively used to refer to the compounds described herein. It is understood that a phosphonic acid will generally have hydrogens associated with two of the phosphonic acid oxygens, and that a phosphonate will generally have other counterions associated with these oxygens. In aqueous solution, hydrogen ions and counterions can exchange rapidly. Thus generally either phosphonic acid and phosphonate compounds can be useful in the invention.

Exemplary alkyl phosphates and alkyl phosphonates include, but are not limited to, an alkyl phosphate or alkyl phosphonate in which the alkyl group is a straight chain unsubstituted alkyl group (e.g., a straight chain alkyl group having from 1 to 26 carbons, e.g., from 8 to 20 carbons, e.g., from 12 to 18 carbons). Additional exemplary alkyl phosphates and alkyl phosphonates include functionalized or substituted alkyl phosphonates and alkyl phosphates, for example, functionalized X-alkyl-phosphonates and X-alkyl-phosphates where X is a terminal group comprising or consisting of a vinyl (CH$_2$), methyl (CH$_3$), amine (NH$_2$), alcohol (CH$_2$OH), epoxide, acrylate, methacrylate, thiol, carboxylate, active ester (NHS-ester), melamine, halide, phosphonate, or phosphate group, or an ethylene glycol (EG) oligomer (EG4, EG6, EG8) or polyethylene glycol (PEG), photoinitiator (e.g., photo-iniferters such as dithiocarbamates (DTC)), photocaged group, or photoreactive group (e.g., psoralen). The alkyl chain spacer in the X-alkyl-phosphonate or X-alkyl-phosphate molecule is a hydrophobic tether that optionally has 1 to 26 methylene (CH$_2$) repeat units, preferably from 8 to 20, and more preferably from 12 to 18. The alkyl chain may contain one or more (up to all) fluorinated groups and/or can instead be a hydrocarbon chain with one or more double or triple bonds along the chain. The X-alkyl-phosphate or X-alkyl-phosphonate layer can furthermore be used as a substrate to anchor other ligands or components of the surface stack, such as a polyelectrolyte multilayer or chemisorbed multilayer. The alkyl phosphates/phosphonates can form a stable, solvent resistant self-assembled monolayer that can protect the underlying material (e.g., aluminum) from corrosion etc.; the role of the alkyl tether in the above structures is to enhance the lateral stability of the chemisorbed monolayer in aqueous environments. In embodiments in which the phosphonate or phosphate compound includes an unsaturated hydrocarbon chain, the double or triple bond(s) can serve as lateral crosslinking moieties to stabilize a self-assembled monolayer comprising the compound.

Specific exemplary alkyl phosphates and alkyl phosphonates include, but are not limited to, octyl phosphonic acid, decyl phosphonic acid, dodecyl phosphonic acid, hexadecyl phosphonic acid, octadecyl phosphonic acid, docosyl phosphonic acid (i.e., C22 phosphonic acid), hydroxy-dodecyl phosphonic acid (HO(CH$_2$)$_{12}$P(O)(OH)$_2$), hydroxy-undecenyl-phosphonic acid, decanediylbis(phosphonic acid), dodecylphosphate, and hydroxy-dodecylphosphate. Ellipsometry and/or contact angle measurements show that octyl phosphonic acid, octadecyl phosphonic acid, hydroxy-dodecyl phosphonic acid, and dodecyl phosphonic acid exhibit specificity toward aluminum/aluminum oxide surfaces relative to Si/SiO$_2$ surfaces. Modification of metal oxides with such phosphates and phosphonates has been described, e.g., in Langmuir (2001) 17:3428, Chem. Mater. (2004) 16:5670; J. Phys. Chem. B (2005) 109:1441, Langmuir (2006) 22:6469, Langmuir (2006) 22:9254, Langmuir (2006) 22:3988, J. Phys. Chem. B (2003) 107:11726, J. Phys. Chem. B (2003) 107:5877, Langmuir (2001) 17:462, J. Phys. Chem. B (2006) 110:25603, Langmuir (2002) 18:3957, Langmuir (2002) 18:3537, and Langmuir (2001) 17:4014.

Metal oxide surfaces can similarly be modified with polyphosphates or polyphosphonates. Chemisorption, e.g., of polyphosphonates differs from the previous description of polyelectrolyte adsorption in that the ligands (phosphonic acid moieties) form a chemical complex with the substrate (e.g., alumina, zirconia, or titania). Such interaction is stronger and less reversible to salt exchange than are simple electrostatic interactions. Examples include, but are not limited to, PEG-phosphonates such as those described in Zoulalian et al. (2006) "Functionalization of titanium oxide surfaces by means of poly(alkyl-phosphonates)" J. Phys. Chem. B 110 (50:25603-25605 or PEG-polyvinyl(phosphonate) copolymers. In general, copolymers including chemisorbing moieties plus PEG or other anti-fouling moieties are contemplated herein.

Other suitable phosphonates include high molecular weight polymeric phosphonates such as polyvinylphosphonic acid (PVPA):

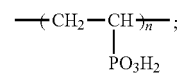

wherein n can be from about 1 to about 1000 or from about 10 to about 100.

Phosphonate end-capped polymers of polymers having acidic functional groups such as carboxylic acids, sulfonic acids and mixtures thereof can also be used. These can include phosphonate end-capped poly(acrylates), poly(sulfonates), and copolymers thereof. Exemplary phosphonate end-capped compounds include:

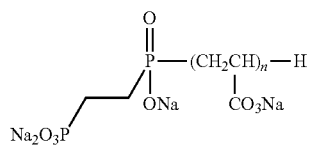

where n can be from about 1 to 1000, can be between about 10 and about 100, and can be about 20 (available from Rhodia, Inc. as AQUARITE EC4020), or

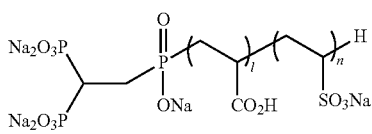

where n and m can be from about 1 to about 1000, from about 10 to about 100, or can each be about 50, in some cases, m is about 24 and n is about 16 (available from Rhodia, Inc. as AQUARITE ESL). Exemplary copolymers copolymer include the copolymers:

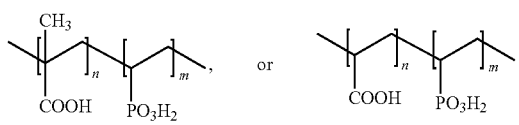

such as vinyl phosphonic acid-acrylic acid copolymers (commercially available from Rhodia as ALBRITECT CP30). The values for n and m can range from about 1 to about 1000. In some cases, m is between about 10 and about 100, and n is between about 100 and 300. In some cases, m is between about 50 and about 70, and n is between about 80 and 120. In some cases, m is about 60 and n is about 200.

Suitable phosphonates also include low molecular weight phosphonates such as 2-carboxyethyl phosphonic acid (also known as 3-phosphonopropionic acid; commercially available from Rhodia as ALBRITECT PM2) and the compounds listed in Table 1 (commercially available as DEQUEST compounds from Solutia, Inc., St. Louis Mo.). Phosphonate compounds can be supplied as salts (e.g., sodium, potassium, lithium, or ammonium salts) or as free acids.

TABLE 1

Exemplary phosphonic acid compounds.

| Chemical Name | Structure |
|---|---|
| Amino tri (methylene phosphonic acid) | [structure] |
| 1-Hydroxy-ethylidene-1,1,-diphosphonic acid | [structure] |
| Hexa-methylene-diaminetetra (methylene-phosphonic acid) | [structure] |
| Diethylene-triamine penta (methylene phosphonic acid) | [structure] |
| ethylene-diamine tetra (methylene phosphonic acid) | [structure] |
| bis(hexa-methylene triamine penta (methylenephosphonic acid)) | |
| Amino methylene phosphonic acid | |
| 2-Phosphono-butane-1,2,4-tricarboxylic acid | [structure] |
| Mono-ethanloamine diphosphonate | |

Suitable polymers for use as passivating agents include polymers produced from the following monomers. Particularly useful polymers comprise polymers with these monomers and also comprising one or more phosphate or phosphonate groups, for example copolymers comprising vinyl (phosphonic acid) (VPA) and at least one other of the monomers listed below.

VPA     VSA

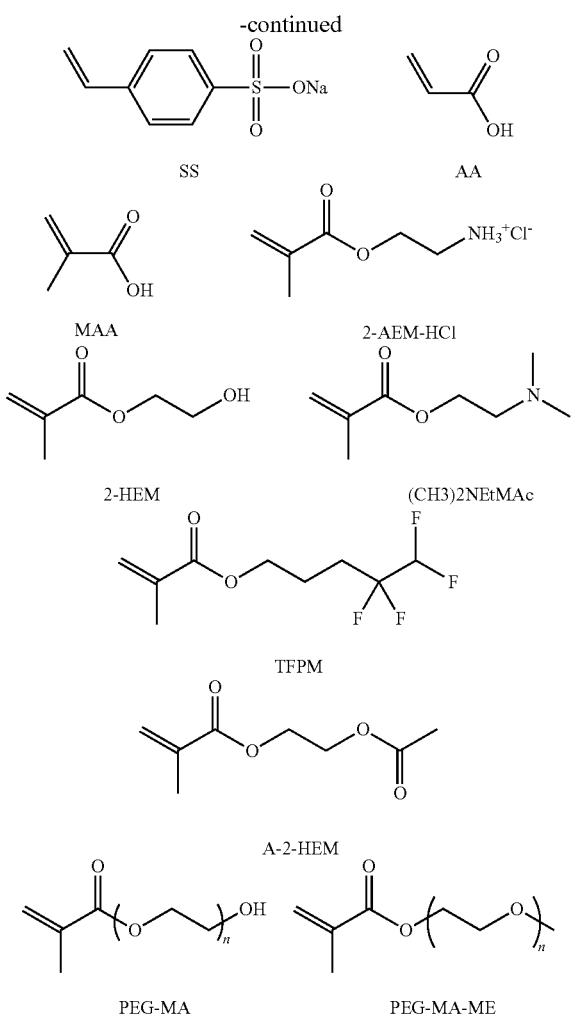

For PEG-MA and PEG-MA-ME, n is generally chosen such that the molecular weight is between about 100 and 10,000 or about 200, 400, or 1000. For example n can be from about 1 to about 1000 or from about 10 to about 100

Examples of other suitable negatively charged passivating agents include, but are not limited to, anionic polyelectrolytes such as poly(styrenesulfonate) and poly(acrylic acid) and macromolecules such as heparin and alginine.

Optionally, positively charged surfaces can be passivated by binding of copolymer structures containing polyelectrolyte blocks (negative) and PEG-ylated blocks. The polyelectrolyte blocks of the copolymer adsorb or anchor the macromolecules to regions of the device that are electropositive (e.g., the aluminum or aluminum oxide areas of a ZMW), and the PEG components provide a non-ionic cushion that precludes the surface attachment or the complexation of the polymerase with the polyelectrolyte blocks. The polyelectrolyte (PE)-PEG copolymers can, for example, be diblock (PEG-PE) or multi-block copolymers (e.g., PE-PEG-PE or PEG-PE-PEG), as well as branched polymers, comb polymers, or dendron-like polymers. While the exemplary copolymers described herein employ PEG, any anti-fouling backbone is applicable, for example, polypyrrolidone, polyvinyl alcohol, dextrans, and polyacrylamides. See, e.g., U.S. patent application publication 2002/0128234, Voros et al. (2003) "Polymer Cushions to Analyze Genes and Proteins" BioWorld 2:16-17, Huang et al. (2002) Langmuir 18(1): 220-230, and Zoulalian et al. (2006) J. Phys. Chem. B 110(51): 25603-25605.

As another example, the surface of the hybrid substrate to which the molecule of interest is not immobilized can be passivated using a polyelectrolyte multilayer. Polyelectrolyte multilayers are conveniently formed through successive deposition of alternating layers of polyelectrolytes of opposite charge. See, e.g., Decher (1997) Science 277:1232.

In one class of embodiments, the phosphate or phosphonate compound serves as the first layer on which a polyelectrolyte multilayer is built on the surface, e.g., by successive deposition of oppositely charged polyelectrolytes.

Selective passivation can be accomplished with multiple layers of phosphorous containing polymers such polymers comprising polyphosphonates. An effective approach to such multilayers uses multivalent cations to assemble the polyphosphonates containing polymers. Particularly useful multivalent cations are those of transition metals, and in particular those of group IV transition metals, titanium (Ti), zirconium (Zr), or hafnium (Hf). A multilayer can be constructed with alternating layers. The multilayers can be produced by alternately treating the surface with a transition metal compound such as $HfCl_2$, $ZrOCl_2$, or $ZrCl_4$, and then with the phosphonate-containing polymer such as PVPA or Cp30. An advantage of a multilayer process is that while the process requires extra steps, it can result in the filling in of defect sites that would be present with a single passivation step.

In some cases, the transition metal compound and conditions can be chosen to have little or substantially no reactivity with $SiO_2$. In other cases, a transition metal compound, e.g. $HfOCl_2$ can be used under conditions where it also reacts with $SiO_2$. This approach can be used, for example where the silica based surface has been functionalized prior to a passivation step. In this case, the transition metal compound may react with any unfunctionalized portions of the silica surface in order to accomplish passivation.

The transition metal compounds can be introduced to the surface in solution, for example in water, methanol or a mixture of water and methanol. The number of layers can be 2, 3, 4, 5, 6, 7, 8, 9, 10 or more than 10 layers. In some embodiments 3 to 6 layers are used.

While polymeric phosphorous containing polymers are generally preferred, in some cases, monomeric compounds such as bisphosphonic acids, alkyl phosphonic acids, or other phosphonic acids can be used. In some cases, the phosphonic acid can incorporate another passivating group such as, for example, ethylene glycol, polyethylene glycol, or carboxylate functionality.

Selective passivation is generally carried out by exposing the substrate surface to a solution comprising the selective passivation compounds mixed with a solvent. The solvent used is typically one that substantially dissolves the passivating compound. The solvents will generally comprise polar solvents. In some cases, an aqueous solvent are preferred. While not being bound by theory, it is believed that the use of an aqueous solvent assists in providing specificity of the passivation to the metal or metal oxide regions. In some cases, the aqueous solvent comprises a mixture of water and an alcohol, for example, water/ethanol or water/methanol. The pH of the solution can affect the level of specificity which is obtained. A pH of between about 0 and 5 is generally used for the passivation reaction. In some cases a pH between about 1 and 4 used. In some cases a pH between about 3 and 4 is used.

The passivation agent, such as PVPA in aqueous solution, can be provided in an aqueous solution at any suitable concentration. The solution can have from about 5% of the passivation agent, to about 95% (w/w or w/v) of passivation agent. The selective passivation reaction can be carried out at a temperature and for a time that will allow for passivation reaction to occur. In some cases, temperatures from 20° C. to 100° C. are used. In some cases, temperatures from 60° C. to 90° C. are used. The reaction times generally range from minutes to hours.

In some cases, the addition of salts can improve the passivation. In some cases, salts having sodium ($Na^+$) are present. In some cases, the addition of bivalent salts such as $Ca^{++}$ can be beneficial with respect to passivation.

It will be understood that the passivation step will often be preceded by one or more washing steps to remove contaminants from the surfaces. Pretreatment steps can also be used, for example to put the metal into the state desired for subsequent reaction. In some cases, a reduction step will be used to produce, for example, a pure metal surface having little or no oxide. In other cases, the surface will intentionally be exposed to an oxidizing environment such as exposure to air in order, for example, to provide a metal having oxide to which a passivating compound can bind.

The level of selective passivation can be evaluated by a variety of techniques that are known in the art of surface characterization. For example, techniques such as X-ray photoelectron spectroscopy (XPS), contact angle, or ellipsometry can be used to characterize the level of selectivity of the coating.

E. Functionalizing the Silica-Based or Transparent Layer

The methods of the invention generally include a step in which the silica-based or transparent layer is functionalized. This functionalization is carried out using a functionalizing agent or coupling agent which reacts with the silica-based or transparent surface. As used herein, a coupling agent is generally a compound that binds to the silica or transparent surface, and also comprises a coupling group that can react with another compound, for example, to bind a molecule of interest such as an enzyme to the surface. A functionalizing agent is a compound that binds to the silica-based or transparent surface that does not necessarily have a separate coupling group for subsequent binding of another compound. The functionalizing agent will generally provide a characteristic or functionality to the silica or transparent region. Such characteristic or functionality could be a chemical or physical characteristic. For example, the functionalizing agent could comprise optically detectable agents that are sensitive to the medium into which the surface is disposed. The terms coupling agent and functionalizing agent are not mutually exclusive. In some cases a functionalizing agent could comprise a reactive group and thus, could be used as a coupling agent.

Coupling of functional groups to the transparent materials may be carried out by any of a variety of methods known in the art. For example, in the context of silica based substrates, e.g., glass, quartz, fused silica, silicon, or the like, well characterized silane chemistries may be used to couple other groups to the surface. Such other groups may include functional groups, activatable groups, and/or linker molecules to either of the foregoing, or the actual molecules of interest that are intended for use in the end application of the surface. In the context of other transparent material types, e.g., polymeric materials, or the like, other processes may be employed, e.g., using hybrid polymer surfaces having functional groups coupled thereto or extending from the polymer surface using, e.g., copolymers with functional groups coupled thereto, metal associative groups, i.e., chelators, thiols, or the like.

Where the transparent material comprises a silica-based surface, silanes (e.g., methoxy-, or ethoxy-, silane reagents) can form stable bonds with silica surfaces via Si—O—Si bond formation, and are less reactive to metal or metal oxide surfaces such as aluminum or aluminum oxide surfaces under appropriately selected reaction conditions (e.g., vapor phase, solution-based treatments). Silanes, for example, silanes modified with coupling groups for attachment of enzymes or other molecules of interest (e.g., biotin-PEG-silanes such as those described in U.S. patent application Ser. No. 11/240,662), can thus be used to bind desired molecules to silica surfaces such as those in a ZMW.

In some cases, the coupling groups are activatable or deactivatable coupling groups. A variety of different activatable or deactivatable coupling groups may be used in conjunction with this aspect of the invention. Typically, such groups include coupling groups that are capped or blocked with a selectively removable group. These include groups that are thermally altered, e.g., thermolabile protecting groups, chemically altered groups, e.g., acid or base labile protecting groups, and photo alterable groups, e.g., photo-cleavable or removable protecting groups. Suitable activatable and deactivatable coupling groups are provided, for example, in U.S. patent application Ser. No. 11/394,352.

A variety of different coupling groups may be used in this context, depending upon the nature of the molecule of interest to be subsequently deposited upon and coupled to the substrate. For example, the coupling groups may include functional chemical moieties, such as amine groups, carboxyl groups, hydroxyl groups, sulfhydryl groups, metals, chelators, and the like. Alternatively or additionally, they may include specific binding elements, such as biotin, avidin, streptavidin, neutravidin, lectins or SNAP-TAGS and their substrates (Covalys Biosciences AG; the SNAP-TAG is a polypeptide based on mammalian O6-alkylguanine-DNA-alkyltransferase, and SNAP-TAG substrates are derivates of benzyl purines and pyrimidines), associative or binding peptides or proteins, antibodies or antibody fragments, nucleic acids or nucleic acid analogs, or the like. Click chemistry including the Azide-Alkyne Huisgen Cycloaddition catalyzed, for example, by copper can also be used.

Additionally, or alternatively, the coupling group may be used to couple an additional group that is used to couple or bind with the molecule of interest, which may, in some cases include both chemical functional groups and specific binding elements. A preferred set of embodiments utilizes biotin to attach a molecule of interest to the silica-based or transparent substrate. The attachment of biotin or other selective binding group to the surface can be accomplished in a number of ways.

One exemplary approach involves reacting a silica-based surface region with a compound having a silane group directly coupled to the selective binding group, for example, a silane-polyethylene glycol-biotin compound to produce a surface having selective binding groups, e.g. biotin bound to the silica-based region. This method provides a one step process for obtaining a silica-based surface having selective binding groups such as biotin attached thereto. In some cases, the silane compound having the selective binding group is diluted with a silane that does not contain the selective binding group, e.g. silane-polyethylene glycol in order to control the density of selective binding groups on the silica-based surface.

Another exemplary approach involves first reacting a silica-based surface with a coupling agent, and reacting the coupling agent on the surface with an attaching agent that has both functionality for reacting with the coupling agent, and functionality for attaching the desired molecule (e.g. a selective binding agent such as. Biotin). For example, the silica-based surface is reacted with an aminosilane or thiol-silane under conditions where the aminosilane or thiol-silane becomes bound to the substrate. The aminosilane or thiol-silane surface is subsequently reacted with an attaching agent, for example having an activated ester coupled to biotin to link the biotin to the aminosilane surface, or a maleimide group coupled to biotin to link to the thiol-silane surface. The attaching agent can be diluted as described herein with molecules that react, for example, with the aminosilane or thiol-silane, but do not have selective binding groups. This process incorporating an attaching group results in the coupling the selective binding agent to the surface in two steps. While this approach uses two steps rather than the one step described above, it can have some advantages in development, processing, and quality control.

The linking chemistry between the coupling agent and the compound having the selective binding agent can comprise any suitable linking chemistry. The linking chemistry can comprise, for example, thiol-maleimide, anhydride-amine, alkyne-azide, epoxide-amine, or amine-activated ester. As with the one step method, the compound having the selective binding agent can be diluted with a compound with the same reactive functionality, but not having the selective binding agent to control the density of selective binding agent on the surface.

In some cases, the compound comprising the selective binding agent is not diluted with another agent such as a capping agent that can bind to the surface, but does not have selective binding agent. Where there is no dilution, a relatively highly density of selective binding agent can be achieved. This high level of selective binding agent allows either for attaching a relatively high density of molecules of interest to the surface, or can be used to attach relatively few molecules of interest to the surface.

In some cases, the compound comprising the selective binding agent is diluted with another agent such as a capping agent that can bind to the surface, but does not have selective binding agent. In accordance with the invention, the low density of the coupling agent on a surface is designed to provide a single reactive moiety within a relatively large area for use in certain applications, e.g., single molecule analyses, while the remainder of the area is substantially non-reactive. As such, coupling groups can be diluted to provide a low density of reactive groups that are typically present on a substrate surface at a density of reactive groups of greater than $1/1 \times 10^6$ nm$^2$ of surface area, but less than about $1/100$ nm$^2$. In more preferred aspects, the density of reactive groups on the surface will be greater than $1/100,000$ nm$^2$, $1/50,000$ nm$^2$, $1/20,000$ nm$^2$ and $1/10,000$ nm$^2$, and will be less than about $1/100$ nm$^2$, $1/1000$ nm$^2$, and $1/10,000$ nm$^2$. For certain preferred applications, the density will often fall between about $1/2500$ nm$^2$ and about $1/300$ nm$^2$, and in some cases up to about $1/150$ nm$^2$.

The conditions for the attachment of the molecule of interest can be controlled such that, for example, only one molecule of interest or one active molecule of interest is delivered to one or more optical confinements on a surface. In some cases, the conditions for the attachment of the molecule of interest are controlled such that 10%, 20%, 30%, 40%, 50%, 60%, 70%, 80%, 90% or more of the optical confinements have only one molecule of interest or one active molecule of interest. Approaches for obtaining a high fraction of optical confinements having one molecule of interest is described in copending U.S. patent application Ser. No. 12/384,097, which is incorporated herein by reference for all purposes.

As another example, negatively charged surfaces can be selectively modified by adsorption of copolymers containing positive polyelectrolyte blocks and PEG-ylated (or similar anti-fouling) blocks. Many silica-based surfaces can be rendered negatively charged under the appropriate conditions in order to facilitate this approach. The polycationic blocks bind to regions of the device that are electronegative, and the PEG components provide a nonreactive surface to preclude non-specific binding. Exemplary polyelectrolyte-PEG copolymers include PLL-PEG (poly(L-lysine)-poly(ethylene glycol)). The PEG groups, or a subset thereof, can include a coupling group such as biotin or the other groups described herein (see, e.g., U.S. patent application publication 2002/0128234 "Multifunctional Polymeric Surface Coatings in Analytic and Sensor Devices" by Hubbell et al., Huang et al. (2002) "Biotin-Derivatized Poly(L-lysine))-g-Poly(ethylene glycol): A Novel Polymeric Interface for Bioaffinity Sensing" Langmuir 18(1): 220-230). Thus, for example, the SiO$_2$ surfaces of a ZMW can be coated with PLL-PEG-biotin, and biotinylated polymerase can then be coupled to the bottom of the ZMW via avidin or streptavidin binding to the PLL-PEG-biotin. Other polycationic blocks can include, for example, PEI (poly(ethylenimine), PDDA (poly(diallyldimethyl ammonium chloride), and PAH (poly(allylamine hydrochloride). In some cases, poly(methyl methacrylate) (PMMA) and copolymers thereof can bee used to functionalize the transparent or silica-based portions of the substrate.

Phospholipid chemistries can also be used to functionalize the surface of the transparent or silica-based portions of the substrate. Chemistries using phospholipid compositions, have shown the ability, in the presence and absence of calcium, to form different levels of supported phospholipid bilayers on metal oxide surfaces and silicon dioxide based surfaces. By selecting the lipid composition and the presence or absence of calcium, one can target deposition of molecules, either as blocking or coupling groups, onto the different surface types. For example, one can select a phospholipid that has high binding selectivity for metal oxide surfaces and use it to block the metal portion of the surface. Alternatively, one can utilize a phospholipid with an appropriate coupling group that has high binding selectivity for the underlying glass substrate, and thus selectively couple additional groups to the surface of the transparent or silica-based portion of the substrate. Examples of these selective phospholipid compositions are described in, e.g., Rossetti, et al., Langmuir. 2005; 21(14):6443-50, which is incorporated herein by reference in its entirety for all purposes.

According to the methods of the invention, the exposure of the transparent or silica-based surface is performed in the presence of passivated opaque or reflective surfaces such as metal or metal oxide surfaces. The treatment of the transparent or silica-based surface can be performed in a selective manner, such that relatively more of the functionalizing agent or coupling agent is bound to the transparent or silica-based surface than is bound to the opaque or reflective surface. The treatment can even be carried out in a highly selective manner, whereby significantly more functionalizing agent or coupling agent is bound to the transparent or silica-based surface than is bound to the opaque or reflective surface. However, we have found that for some applications, such as many single-molecule detection applications, even a highly selective treatment will result in more functionalizing agent or coupling agent bound to the opaque or reflective area than is desired. Where this is the case, a subsequent selective removal step can be employed to remove the unwanted groups from the opaque or reflective regions.

F. Selective Removal of Coupling Agent or Functionalizing Agent

We have found that surfaces having the desired low level of functionalizing agent or coupling agent bound to the opaque or reflective regions can be obtained by following the steps described above followed by a step involving the selective removal of unwanted functionalizing agent or coupling agent from the opaque or reflective regions while removing little to no functionalizing agent or coupling agent from the transparent or silica-based regions. The use of a selective removal step can allow for the use of less-specific chemistry for functionalizing the transparent or silica surfaces than might otherwise be used without the selective removal step.

The selective removal compounds of the invention will generally remove or deactivate a significant portion of the functionalizing agent or coupling agent that is bound to, or otherwise associated with the passivated opaque or reflective surfaces of the substrate. In some embodiments, the selective removal agent will remove or deactivate substantially all of the functionalizing agent or coupling agent bound or associated with the passivated opaque or reflective surfaces of the substrate. The deactivation of the functionalizing agent can occur in various ways. Deactivation of the functionalizing agent can include chemical reaction with the functionalizing agent, and can include covering or sequestering the functionalizing agent. In some embodiments the selective removal agent will remove or deactivate greater than 99.9%, greater than 99%, greater than 98%, greater than 95%, greater than 90%, greater than 80%, greater than 75%, greater than 70% or greater than 60% of the functionalizing agent or coupling agent that is bound to, or otherwise associated with the passivated opaque or reflective surfaces of the substrate.

A suitable selective removal agent will leave enough functionalizing agent on the transparent or silica-based surface to allow for the substrate to function, e.g. for molecular analysis. In some embodiments, the selective removal agent will remove little or no functionalizing agent or coupling agent from the transparent or silica-based surfaces. In some embodiments, the selective removal agent will remove substantially no functionalizing agent or coupling agent from the transparent or silica-based surfaces of the substrate. In some embodiments the functionalizing agent will remove less than 0.1%, less than 1%, less than 2%, less than 5%, less than 10%, less than 15%, less than 20%, less than 25%, less than 30%, or less than 50% of the functionalizing agent or coupling agent from the transparent or silica-based surfaces of the substrate.

Suitable selective removal agents include acidic compounds, for example, compounds having one or more functional groups with a pKa of less than about 6, less than about 5, less than about 4, less than about 2, less than about 1 or lower than 1. We have found that the acidic selective removal agents are particularly useful where the opaque or reflective layer comprises a metal or metal oxide, for example aluminum or aluminum oxide.

The selective removal agents include compounds having, for example carboxylic acid (—CO$_2$H), sulfonic acid (—SO$_3$H), phosphonate (—PO$_3$H$_2$), or phosphate (—OPO$_3$H$_2$) functional groups or combinations thereof.

Particularly useful selective removal agents comprise polymers having acidic functionality. These polymers include, for example, carboxylic acid groups, e.g. acrylates, including poly(acrylic acid) (PAA), and poly(methacrylic acid), sulfonic acid groups, e.g. poly(vinylsulfonic acid) (PVSA), phosphonic acid groups, e.g. poly(vinylphosphonic acid) (PVPA), or phosphoric acid groups or copolymers having two or more of these groups.

While not to be bound by theory, it is believed that the polymeric selective removal agents are beneficial in some cases because they can effectively remove functionalizing agents or coupling agents from the passivated opaque or reflective surfaces, yet because of their higher molecular weight, will not diffuse through a passivation layer to react with the underlying opaque or reflective layer, causing unwanted reactions, for example corrosion, especially in the case of a metal layer. In some cases it is desirable to minimize or eliminate corrosion, which can remove the passivation layer on the opaque or reflective layer, and can result in removal of portions of the layer, causing pitting, and changing its dimensions, e.g. thinning the layer, and enlarging apertures.

The number average molecular weight (Mn) of the polymeric selective removal agents can be from about 1,000 to about 100,000 or from about 5,000 to about 50,000.

Polymeric selective removal agents can comprise poly(vinylsulfonic acid) PVSA, having the structure:

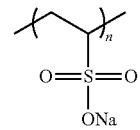

Poly(vinylsulfonic acid)
(PVSA)

wherein n can be about 1 to about 1000, or about 10 to about 100. In some cases, n is selected to provide a suitable molecular weight for acting as a selective removal agent. In the molecular weight is from about 1,000 to about 100,000 or from about 1,000 to about 50,000. In some embodiments, the PVSA has a number average molecular weight of Mn from about 4,000 to about 9,000. In some embodiments the PVSA has a polydispersity from about 1.2 to about 1.6.

Selective removal agents of the invention can also comprise poly(styrenesulfonic acid) (PSSA), and poly(styrenesulfonic acid-co-maleic acid) (PSSA-MA) with the structures shown below.

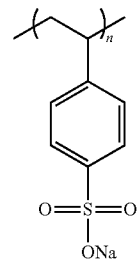

Poly(stryenesulfonic acid)
(PSSA)

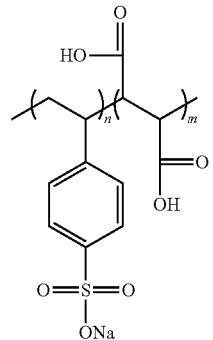

Poly(stryenesulfonic acid-co-maleic acid)
(PSSA-MA)

wherein n and m are selected to provide a suitable molecular weight for acting as a selective removal agent. In some cases n and m are from 1 to about 1000. In some cases, m and n are from about 10 to about 500.

Suitable copolymers include compounds comprising PAA-PVSA, PAA-PVPA, PVSA-PVPA. In some cases, the polymer or copolymer selective removal agents have attached to them polyethylene glycol, creating PEG-ylated polymers.

One class of selective removal agents comprise compounds having the structure below:

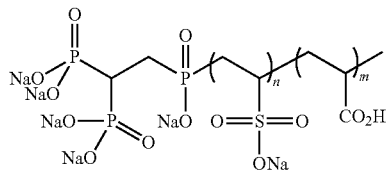

wherein n and m are selected to provide a suitable molecular weight for acting as a selective removal agent. In some embodiments, n is from about 1 to about 1000, and m is from about 1 to about 1000. In some embodiments, n is from about 10 to about 100, and m is from about 10 to about 100. In some embodiments n is about 50 and m is about 50. One preferred embodiment comprises AQUARITE ESL, available from Rhodia, Inc.

Other exemplary copolymers which comprise selective removal agents of the invention include the copolymers below:

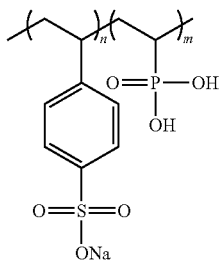

Poly(stryenesulfonic acid-co-phosphonic acid)
(PSSA/PVPA)

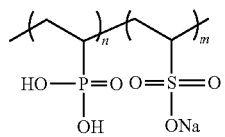

Poly(sulfonic acid-co-phosphonic acid)
(PVSA/PVPA)

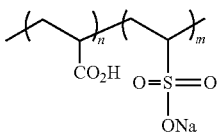

Poly(sulfonic acid-co-acrylic acid)
(PVSA/PAA)

and

-continued

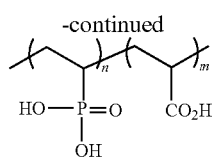

(PVPA/PAA)

wherein n and m are selected to provide a suitable molecular weight for acting as a selective removal agent. In some embodiments, n is from about 1 to about 1000, and m is from about 1 to about 1000. In some embodiments, n is from about 10 to about 100, and m is from about 10 to about 100.

For copolymers described herein having two polymeric regions, the ratio of the regions can be about 10:90, 20:80, 30:70, 40:60, 50:50, 60:40, 70:30, 80:20, or 90:10 (molar or weight ratio).

Suitable materials for use as a selective removal agent include DEQUEST compounds available from ThermPhos Trading GmbH; including, for example, DEQUEST P9000 a homopolymer of maleic acid, DEQUEST P9020, a modified polyacrylic acid, sodium salt, and DEQUEST P9030, a sulphonated polyacrylic acid copolymer.

Generally, corrosion of the opaque or reflective layer is undesirable, and should be minimized or eliminated. However, there are certain instances, such as those for creating an island of functionalizing agent or coupling agent as described in U.S. patent application Ser. No. 12/384,097, filed Mar. 30, 2009, where corrosion, if controlled, can be beneficial.

The substrates can be treated with the selective removal agents using methods described herein and methods known in the art. The selective removal agents are typically delivered to the substrates in solution, but other methods of delivery, such as delivery of the selective removal agents in a gaseous form can be used. The solutions of the selective removal agent for treatment of the substrate will generally utilize solvents in which the selective removal agent is substantially soluble. In some cases aqueous solutions are used.

An exemplary method of treating the substrate with selective removal agents comprises putting a solution containing the selective removal agent into contact with the substrate and bringing the solution to a temperature for a period of time. In some cases agitation or stirring of the solution is carried out during such time. The solution is then removed, after which the substrate may be rinsed, for example, with pure solvent, e.g. pure water, and dried.

The concentration of the selective removal agent will typically be between 0.01% and 20% (weight by volume, e.g. g/mL). In many cases the concentration of the selective removal agent will be less than 1%, for example between 0.1% and 0.8% or between 0.2% and 0.6%.

The treatment with selective removal agent is generally carried out under acidic conditions, e.g. at a pH of less than 6. In some cases it is carried out at a pH of less than 5, less than 4, less than 3, less than 2, less than 1, or lower. The treatment with selective removal agent can be carried out at between pH 6 and pH 0, between pH 5 and pH 1, between pH 4 and pH 2. We have found that in some cases, the selective removal reaction tends to proceed more rapidly at lower pH. In some cases, if the pH is too low, it is difficult to control the level of corrosion. The reaction can be carried out at any effective temperatures. For example, temperatures from 20° C. to 100° C. can be employed. In some cases temperatures between 40° C. and 95° C. are used. In some cases, temperatures between 80° C. and 90° C. are used. The time for the selective removal reaction is generally between 1 minute and 1 day. The optimal time may vary depending, for example, on the pH and temperature employed. Times between about 10 min. to about 120 min., or between about 20 min. and about 60 min. can be used.

In some cases, the addition of salts can improve the selective removal reaction. In some cases, salts having sodium (Na$^+$) are present. In some cases, the addition of bivalent salts such as Ca$^{++}$ can be beneficial with respect to selective removal.

In one exemplary embodiment the substrate is a fused silica lower layer having an aluminum cladding layer disposed upon the fused silica layer, and having a series of apertures having diameters between 30 nm and 200 nm extending through the aluminum cladding layer. The aluminum cladding layer is exposed to air such that the surface of the aluminum would comprise aluminum oxide. The substrate is immersed in an aqueous solution comprising a phosphonate containing polymer such as AQUARITE CP-30 or PVPA, heated, and with deionized water. This treatment results in the selective coating of the aluminum portions of the surface of the substrate. The substrate is then immersed in a solution of silane coupling agent and treated in a manner such that the silane coupling agent becomes bound to the fused silica portions of the surface. While the silica binds preferentially to the fused silica surface as compared to the passivated aluminum surface, there is a measurable amount of silane coupling agent bound to the aluminum regions. The substrate is submersed into an aqueous solution of selective removal agent, e.g. PVSA, and heated. The substrate is rinsed with deionized water and dried. The resulting surface may have a high density of coupling agent on the fused silica regions, and very low to undetectable amounts of coupling agent on the aluminum portions.

While not being bound by theory, it is believed that where silane functionalizing agents or silane coupling agents are used, that in some cases, the selective removal agent acts by the selective scission of P—O—Si, and/or Metal-O—Si (e.g. Al—O—Si) bonds on metal portions of the substrate while not reacting with, or reacting slowly with the Si—O—Si bonds connecting the silanes to the silica surface.

G. Molecules of Interest-Attachment

The methods described herein can be used, for example, for the selective attachment of one or molecules of interest to a transparent or silica-based region of the surface of a substrate. These molecules of interest can thereby be disposed into reaction and or observation regions, such as within an optical confinement.

The molecules of interest are generally attached to the coupling agents selectively placed onto the transparent or silica-based portions of the surface as described above. A variety of chemistries are available for specifically attaching a molecule of interest to the coupling agents bound to the surface.

For example, where biotin is bound to the transparent or silica-based regions of the surface, this surface can be used to attach the molecule of interest using a binding agent such as streptavidin, which has a very high affinity for biotin. In one approach, the molecule of interest has a biotin tag which can then be attached to the surface using an intermediate binding agent, e.g., streptavidin, which acts to bind to both the surface and the molecule of interest. In another approach, streptavidin is attached directly to the molecule of interest.

A variety of analytes can be delivered to reaction/observation regions using the methods and compositions herein. These include enzyme substrates, nucleic acid templates, primers, etc., as well as polypeptides such as enzymes (e.g., polymerases).

A wide variety of nucleic acids can be analytes in the methods herein. These include cloned nucleic acids (DNA or RNA), expressed nucleic acids, genomic nucleic acids, amplified nucleic acids cDNAs, and the like. Details regarding nucleic acids, including isolation, cloning and amplification can be found, e.g., in Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc; Kaufman et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley).

Similarly, a wide variety of proteins, e.g., enzymes, can also be delivered using the methods herein. A variety of protein isolation and detection methods are known and can be used to isolate enzymes such as polymerases, e.g., from recombinant cultures of cells expressing the recombinant polymerases of the invention. A variety of protein isolation and detection methods are well known in the art, including, e.g., those set forth in R. Scopes, *Protein Purification*, Springer-Verlag, N.Y. (1982) and *Handbook of Bioseparations*, Academic Press (2000). Sambrook, Ausubel, Kaufman, and Rapley supply additional useful details.

For a description of polymerases and other enzymes that are active when bound to surfaces, which is useful in single molecule sequencing reactions in which the enzyme is fixed to a surface (e.g., to a particle or to a wall of a reaction/observation region, e.g., in a ZMW), e.g., conducted in a ZMW, see Hanzel et al. ACTIVE SURFACE COUPLED POLYMERASES, WO 2007/075987 and Hanel et al. PROTEIN ENGINEERING STRATEGIES TO OPTIMIZE ACTIVITY OF SURFACE ATTACHED PROTEINS, WO 2007/075873). For a description of polymerases that can incorporate appropriate labeled nucleotides, useful in the context of sequencing, see, e.g., Hanzel et al. POLYMERASES FOR NUCLEOTIDE ANALOGUE INCORPORATION, WO 2007/076057. For further descriptions of single molecule sequencing applications utilizing ZMWs, see Levene et al. (2003) "Zero Mode Waveguides for single Molecule Analysis at High Concentrations," *Science* 299:682-686; Eid et al. (2008) "Real-Time DNA Sequencing from Single Polymerase Molecules" *Science DOI:* 10.1126/science. 322.5905.1263b; Korlach et al. (2008) "Selective aluminum passivation for targeted immobilization of single DNA polymerase molecules in zero-mode waveguide nanostructures" *Proceedings of the National Academy of Sciences U.S.A.* 105(4): 1176-1181; Foquet et al. (2008) "Improved fabrication of zero-mode waveguides for single-molecule detection" *Journal of Applied Physics* 103, 034301; "Zero-Mode Waveguides for Single-Molecule Analysis at High Concentrations" U.S. Pat. No. 7,033,764, U.S. Pat. No. 7,052, 847, U.S. Pat. No. 7,056,661, and U.S. Pat. No. 7,056,676, the full disclosures of which are incorporated herein by reference in their entirety for all purposes. In some cases, the enzyme can be covalently attached to the substrate through functional groups on the enzyme such as amine, carboxylate, or thiol groups, for example with NHS or maleimide linking chemistry.

In order to attach an enzyme to the surface, binding elements can be added to the polymerase (recombinantly or, e.g., chemically) including, e.g. biotin, avidin, GST sequences, modified GST sequences, e.g., that are less likely to form dimers, biotin ligase recognition (BiTag) sequences, S tags, SNAP tags SNAP-TAGS (polypeptides based on mammalian O6-alkylguanine-DNA-alkyltransferase), enterokinase sites, thrombin sites, antibodies or antibody domains, antibody fragments, antigens, receptors, receptor domains, receptor fragments, ligands, dyes, acceptors, quenchers, or combinations thereof.

Multiple surface binding domains can be added to orient the polypeptide relative to a surface and/or to increase binding of the polymerase to the surface. By binding a surface at two or more sites, through two or more separate tags, the polymerase is held in a relatively fixed orientation with respect to the surface. Further details on attaching tags is available in the art. See, e.g., U.S. Pat. Nos. 5,723,584 and 5,874,239 for additional information on attaching biotinylation peptides to recombinant proteins.

In some cases the desired molecule or molecule of interest can be attached to the surface in a one step process in which a coupling group, for example biotin, is bound to the transparent or silica based portion of the surface, and the The attached molecule of interest can then be observed using the optical containments to characterize its behavior.

H. Substrates Having High Levels of Bias

The methods of the invention can be used to produce substrate surfaces having high levels of bias. The term bias as used herein is generally used to refer a measure of a difference in surface properties of two different surfaces or two different portions of a surface. The measured bias can represent the selective attachment of an agent to one portion of the surface over another portion of the surface. The bias can be represented as a ratio of a property associated with the agent on one portion of the surface to that measured on a different portion of the surface. It will be understood that there may be multiple methods for measuring bias, and that the bias measured by one method may not provide the same level of bias as another method. Bias can be measured, for example, using optical methods (including fluorescence), X-ray photoelectron spectroscopy XPS), ellipsometry, or contact angle.

The methods of the invention provide for producing substrates having surfaces with high bias. In particular, the substrates of the invention can have a transparent or silica-based surface portion and an opaque or reflective surface portion, wherein the bias for agents bound to one portion as compared to the other portion is high. Substrates having these characteristics can be, for example, arrays of optical confinements. In some cases, the level of bias can be measured on the array of optical confinements. In some cases, it is not practical to measure the bias on the array of optical confinements. In such cases, the bias that is achievable by a surface preparation method can be determined on a surrogate surface. For example, where the array of optical confinements comprises a fused silica layer having a metal cladding layer having nanometer scale apertures through the cladding, the amount of fused silica available for the measurement can be small, making the measurement of bias difficult. In such cases, coupons of fused silica coupons having regions of metal coated on their top surfaces can be used to determine the bias that is obtained by a method of the invention.

In some cases, the bias represents the relative levels of a coupling agent on the transparent or silica-based portions of the substrate as compared to the levels of coupling agent on the opaque or reflective portions of the substrate. In these cases, bias can be determined by measuring the amount of attachment of a compound that reacts with the coupling agent. Examples of chemistries that can be used for coupling groups and compounds that react with the coupling groups described herein. Other chemistries are well known in the art. In some cases, the coupling agent can comprise a selective binding agent.

In some cases, the bias represents the relative levels of a selective binding agent on the transparent or silica-based portions of the substrate as compared to the levels of selective binding agent on the opaque or reflective portions of the substrate. For example, where the selective binding agent is biotin, bias can be determined by measuring the relative amount of a labeled avidin, streptavidin, or neutravidin bound to each surface region. In some cases, for example where fluorescent labels are used, a metal or metal oxide surface may tend to quench the fluorescence of the labeled avidin, streptavidin, or neutravidin. In these cases, the labeled avidin, streptavidin, or neutravidin can be bound to beads, allowing for fluorescence in the bound state.

The bias for a substrate treated with a selective binding agent can also be determined using a molecule of interest, e.g. an enzyme of interest that is labeled. The enzyme of interest can be labeled covalently, or the enzyme could be labeled by having the enzyme bound to a molecule that is labeled. For example, the enzyme could be bound to a labeled substrate molecule. Where the enzyme of interest is a polymerase, the polymerase can be bound to a fluorescently labeled template nucleic acid. For example, a surface having been selectively functionalized with a biotin containing selective binding agent as described herein can be reacted first with neutravidin, and then with an enzyme bound to a fluorescently bound template where the enzyme comprises a biotin group. The relative fluorescence measured on the transparent or silica based portions of the surface relative to that on the opaque or reflective portions provides a measure of the bias.

In one aspect, the invention provides an array of optical confinements having a surface with both a silica-based and a metal or metal-oxide portion, wherein the array has been treated with a passivating agent and a coupling agent, wherein when a coupon having regions with the same type of silica as the silica-based portions and the same type of metal or metal-oxide as the metal or metal oxide portions as the array is treated in the same manner as the array, the coupon exhibits a fluorescent intensity bias of greater than about 5, greater than about 8, greater than about 10, greater than about 20, greater than about 30, greater than about 40, greater than about 50, greater than about 60, greater than about 70, greater than about 80, greater than about 90, or greater than about 100 in a fluorescent bias assay such as a neutravidin labeled bead assay. The coupling agent can comprise a selective binding agent such as biotin.

In one aspect, the invention provides an array of optical confinements having a surface with both a silica-based and a metal or metal-oxide portion, wherein the array has been treated with a passivating agent and a coupling agent, wherein when a coupon having regions with the same type of silica as the silica-based portions and the same type of metal or metal-oxide as the metal or metal oxide portions as the array is treated in the same manner as the array, the coupon exhibits a fluorescent intensity bias of greater than about 5, greater than about 8, greater than about 10, greater than about 20, greater than about 30, greater than about 40, greater than about 50, greater than about 60, greater than about 70, greater than about 80, greater than about 90, or greater than about 100 in a labeled enzyme assay. The coupling agent can comprise a selective binding agent such as biotin.

In one aspect, the invention provides an array of optical confinements having a surface with both a silica-based and a metal or metal-oxide portion, wherein the array has been treated with a phosphorous containing passivating agent and a coupling agent; wherein when a coupon having regions with the same type of silica as the silica-based portions and the same type of metal or metal-oxide as the metal or metal oxide portions as the array is treated in the same manner as the array, the metal or metal oxide portion of the coupon exhibits an XPS signal for phosphorous of, greater than about 10, greater than about 20, greater than about 30, greater than about 40, greater than about 50, greater than about 60, greater than about 70, greater than about 80, greater than about 90, or greater than about 100 times phosphorous signal on the transparent, or silica based portion of the coupon.

In one aspect, the invention provides an array of optical confinements having a surface with both a silica-based and a metal or metal-oxide portion, wherein the array has been treated with a passivating agent and a coupling agent; wherein when a coupon having regions with the same type of silica as the silica-based portions and the same type of metal or metal-oxide as the metal or metal oxide portions as the array is treated in the same manner as the array, the coupon exhibits an ellipsometric bias of greater than about 10, greater than about 20, greater than about 30, greater than about 40, greater than about 50, greater than about 60, greater than about 70, greater than about 80, greater than about 90, or greater than about 100. The coupling agent can comprise a selective binding agent such as biotin.

I. Lipid Bilayer Functionalization of Optical Confinements

An aspect of the invention is the functionalization of the transparent or silica-based portions of the substrate surface with a lipid bilayer. The lipid bilayer can then be used to immobilize the molecule of interest within the optical confinement.

By choosing the appropriate conditions, the lipid bilayer can be formed by self-assembly onto the transparent or silica-based surface. Conditions can be chosen such that the lipid bilayer will form selectively on the transparent or silica based surfaces and not on the opaque or reflective surfaces of an array of optical confinements. For example, an array of optical confinements having a metal cladding layer on a silica-based surface can be treated by the methods described herein to selectively passify the metal cladding layer. The pacified metal cladding layer can be produced to have different chemical and physical properties that the silica-based portion, e.g. positive vs. negative, or neutral vs. negative, such that the lipid bilayer will form only on the, e.g. negatively charged, silica layer.

A lipid bilayer is a thin membrane made of two layers of lipid molecules. Any suitable lipid or mixture of lipids can be used to functionalize the optical confinement such as a ZMW. Suitable bilayers include those made mostly of phospholipids, which have a hydrophilic head and two hydrophobic tails. When phospholipids are exposed to water, they tend to arrange themselves into a two-layered sheet (a bilayer) with their tails pointing toward the center of the sheet. In some cases, a positively charged head group of the phospholipid can associate with negative groups on the transparent or silica based surface, thereby anchoring the lipid bilayer to the surface. The bilayers used in the invention may also include other molecules which can improve the stability of the bilayer, such as, for example molecules of cholesterol.

Suitable lipids include phospholipids including phosphatidylcholine, phosphatidylserine, phosphatidylethanolamine, and phosphatidylglycerol. The lipids can comprise a zwitterionic headgroup, such as that in phosphatidylcholine, which has a negative charge on the phosphate group and a positive charge on the amine but, because these local charges balance, having no net charge. In other cases, lipids having a net positive or net negative charge can be used. Mixtures of lipids having different net charges can also be used.

Any suitable lipids that can form a lipid bilayer, either alone or in combination with other lipids can be used. Suitable lipids include fatty acids, glycerolipids, glycerophospholipids, sphingolipids, sterol lipids, prenol lipids, saccharolipids, and polyketides. Suitable lipids include monoglycerides, diglycerides, and triglycerides.

Figure 7:
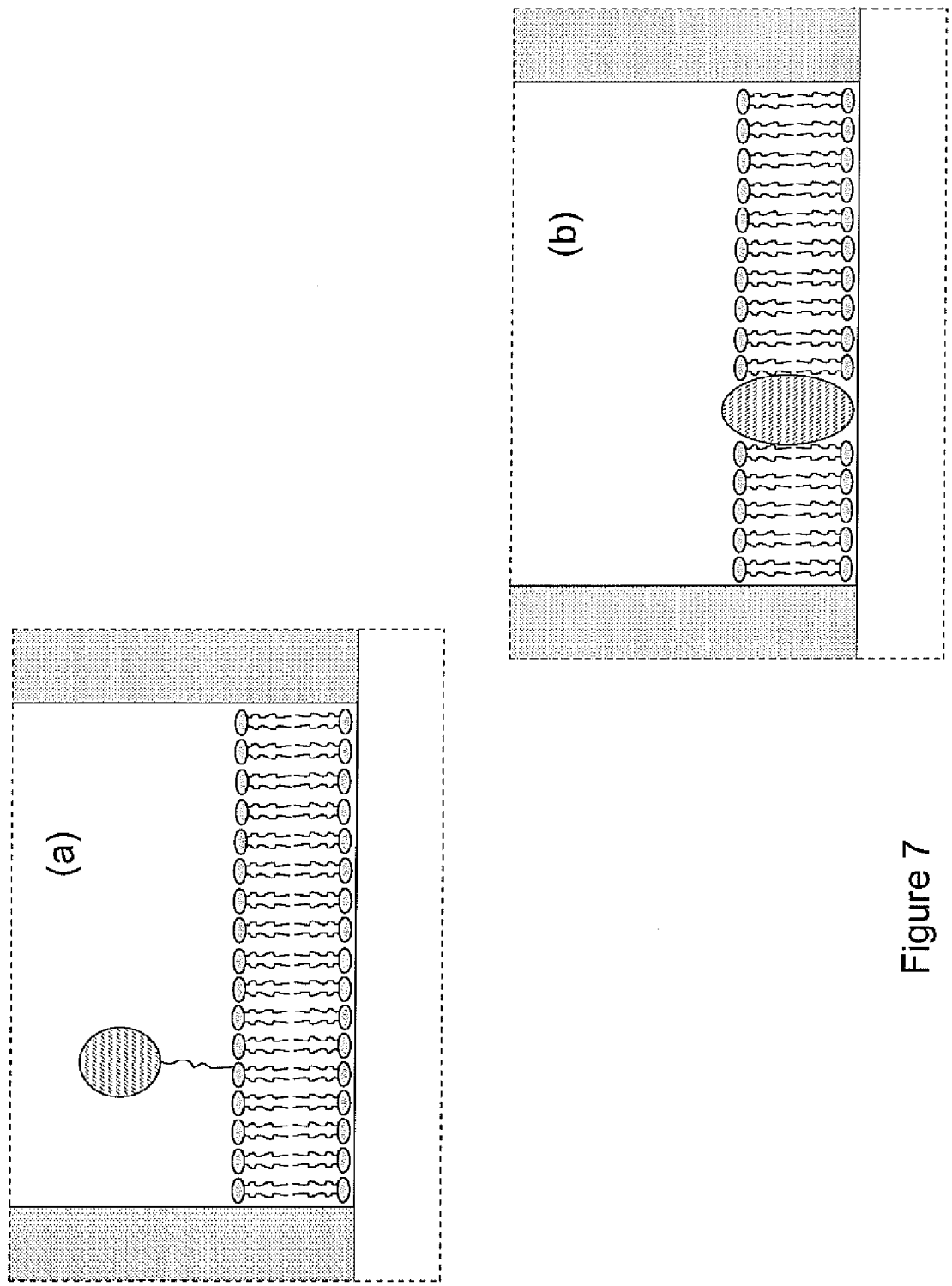
FIG. 7 shows a schematic illustration of an optical confinement of the invention having a lipid bilayer coating on a transparent or silica-based region.

The molecule of interest can be attached to or associated with the lipid bilayer. For example, the molecule of interest, for instance an enzyme or other protein, can be attached to one or more lipid components which will serve to bind or associate the molecule of interest with the lipid bilayer. The tether can be constructed such that the molecule of interest is held within the observation region of the optical confinement. FIG. 7(a) shows an optical confinement having a silica base layer and an aluminum cladding with a lipid bilayer disposed upon the silica surface. The molecule of interest, e.g. an enzyme such as a polymerase, is tethered to a lipid forming component, thus attaching the enzyme to the bilayer and to the base of the optical confinement, for example ZMW.

The tether can either be short, having just a few atoms in the linking group, or can be long, such as a polymeric tether. The tether will generally comprise water soluble functional groups. The linker can comprise, for example polyethylene glycol. The tether can be made of other water soluble functionality, for example, polymers with ether, hydroxyl, carboxyl, amine, sugar, or sulfonate functionality. The tether will generally be from 1 nm to about 50 nm in length.

The structure having the molecule of interest tethered to the lipid bilayer can be formed by a variety of methods. In one method, the lipid membrane is disposed upon the base of the optical confinement, and the lipid membrane has a functionalized tether attached to it. Subsequently, the molecule of interest, having a group that is reactive to the functionalized tether is added. Chemistries for attaching the molecule of interest to the functionalized tether include the chemistries described herein for coupling agents (e.g. maleimide, thiol, amine) and selective binding agents (e.g. biotin). Alternatively, the membrane can first be formed on the optical confinement, and the molecule of interest attached via a tether to a lipid associating component (e.g. a lipid or membrane protein) can be subsequently added.

In some cases, the molecule of interest can be associated directly with the lipid bilayer. FIG. 7(b) shows an optical confinement wherein the molecule of interest is disposed within the lipid bilayer. The lipid bilayer is generally hydrophobic in its interior. Some proteins, e.g. membrane proteins, have hydrophobic portions which result in their association with membranes. In some cases, the molecule of interest will comprise a membrane protein, which will thermodynamically associate with the membrane. In other cases, the molecule of interest can be modified, for example by mutation or with the attachment of hydrophobic moieties such that it will associate with the enzyme. The molecule of interest can alternatively be attached to a membrane protein, for example in the form of a fusion protein.

In some cases the attachment of the molecule of interest can be carried out such that some or all of the optical confinements on the optical confinement array have one molecule of interest per optical confinement.

III. Apparatus

In certain preferred embodiments, the substrates of the present invention comprise arrays of optical confinements that are monitored using an optical system capable of detecting and/or monitoring interactions between reactants at the single-molecule level. Such an optical system achieves these functions by first generating and transmitting an incident wavelength to the reactants, followed by collecting and analyzing the optical signals from the reactants. Such systems typically employ an optical train that directs signals from the reactions to a detector, and in certain embodiments in which a plurality of reactions is disposed on a solid surface, such systems typically direct signals from the solid surface (e.g., array of confinements) onto different locations of an array-based detector to simultaneously detect multiple different optical signals from each of multiple different reactions. In particular, the optical trains typically include optical gratings or wedge prisms to simultaneously direct and separate signals having differing spectral characteristics from each confinement in an array to different locations on an array based detector, e.g., a CCD, and may also comprise additional optical transmission elements and optical reflection elements.

An optical system applicable for use with the present invention preferably comprises at least an excitation source and a photon detector. The excitation source generates and transmits incident light used to optically excite the reactants in the reaction. Depending on the intended application, the source of the incident light can be a laser, laser diode, a light-emitting diode (LED), a ultra-violet light bulb, and/or a white light source. Further, the excitation light may be evanescent light, e.g., as in total internal reflection microscopy, certain types of waveguides that carry light to a reaction site (see, e.g., U.S. Application Pub. Nos. 20080128627, 20080152281, and 200801552280), or zero mode waveguides, described below. Where desired, more than one source can be employed simultaneously. The use of multiple sources is particularly desirable in applications that employ multiple different reagent compounds having differing excitation spectra, consequently allowing detection of more than one fluorescent signal to track the interactions of more than one or one type of molecules simultaneously. A wide variety of photon detectors or detector arrays are available in the art. Representative detectors include but are not limited to optical reader, high-efficiency photon detection system, photodiode (e.g. avalanche photo diodes (APD)), camera, charge couple device (CCD), electron-multiplying charge-coupled device (EMCCD), intensified charge coupled device (ICCD), and confocal microscope equipped with any of the foregoing detectors. For example, in some embodiments an optical train includes a fluorescence microscope capable of resolving fluorescent signals from individual sequencing complexes. Where desired, the subject arrays of optical confinements contain various alignment aides or keys to facilitate a proper spatial placement of the optical confinement and the excitation sources, the photon detectors, or the optical train as described below.

The subject optical system may also include an optical train whose function can be manifold and may comprise one or more optical transmission or reflection elements. Such optical trains preferably encompass a variety of optical devices that channel light from one location to another in either an altered or unaltered state. First, the optical train collects and/or directs the incident wavelength to the reaction site (e.g., optical confinement). Second, it transmits and/or directs the optical signals emitted from the reactants to the photon detector. Third, it may select and/or modify the optical properties of the incident wavelengths or the emitted wavelengths from the reactants. In certain embodiments, the optical train controls an on/off cycle of the illumination source to provide illuminated and non-illuminated periods to one or more illuminated reaction sites. Illustrative examples of such optical transmission or reflection elements are diffraction gratings, arrayed waveguide gratings (AWG), optic fibers, optical switches, mirrors (including dichroic mirrors), lenses (including microlenses, nanolenses, objective lenses, imaging lenses, and the like), collimators, optical attenuators, filters (e.g., polarization or dichroic filters), prisms, wavelength filters (low-pass, band-pass, or high-pass), planar waveguides, wave-plates, delay lines, and any other devices that guide the transmission of light through proper refractive indices and geometries. One example of a particularly preferred optical train is described in U.S. Patent Pub. No. 20070036511, filed Aug. 11, 2005, and incorporated by reference herein in its entirety for all purposes.

In a preferred embodiment, a reaction site (e.g., optical confinement) containing a reaction of interest is operatively coupled to a photon detector. The reaction site and the respective detector can be spatially aligned (e.g., 1:1 mapping) to permit an efficient collection of optical signals from the reactants. In certain preferred embodiments, a reaction substrate is disposed upon a translation stage, which is typically coupled to appropriate robotics to provide lateral translation of the substrate in two dimensions over a fixed optical train. Alternative embodiments could couple the translation system to the optical train to move that aspect of the system relative to the substrate. For example, a translation stage provide a means of removing a reaction substrate (or a portion thereof) out of the path of illumination to create a non-illuminated period for the reaction substrate (or a portion thereof), and returning the substrate at a later time to initiate a subsequent illuminated period. An exemplary embodiment is provided in U.S. Patent Pub. No. 20070161017, filed Dec. 1, 2006.

In particularly preferred aspects, such systems include arrays of reaction regions, e.g., zero mode waveguide arrays, that are illuminated by the system, in order to detect signals (e.g., fluorescent signals) therefrom, that are in conjunction with analytical reactions being carried out within each reaction region. Each individual reaction region can be operatively coupled to a respective microlens or a nanolens, preferably spatially aligned to optimize the signal collection efficiency. Alternatively, a combination of an objective lens, a spectral filter set or prism for resolving signals of different wavelengths, and an imaging lens can be used in an optical train, to direct optical signals from each confinement to an array detector, e.g., a CCD, and concurrently separate signals from each different confinement into multiple constituent signal elements, e.g., different wavelength spectra, that correspond to different reaction events occurring within each confinement.

The systems of the invention also typically include information processors or computers operably coupled to the detection portions of the systems, in order to store the signal data obtained from the detector(s) on a computer readable medium, e.g., hard disk, CD, DVD or other optical medium, flash memory device, or the like. For purposes of this aspect of the invention, such operable connection provide for the electronic transfer of data from the detection system to the processor for subsequent analysis and conversion. Operable connections may be accomplished through any of a variety of well known computer networking or connecting methods, e.g., Firewire®, USB connections, wireless connections, WAN or LAN connections, or other connections that preferably include high data transfer rates. The computers also typically include software that analyzes the raw signal data, identifies signal pulses that are likely associated with incorporation events, and identifies bases incorporated during the sequencing reaction, in order to convert or transform the raw signal data into user interpretable sequence data (See, e.g., Published U.S. Patent Application No. 2009-0024331, the full disclosure of which is incorporated herein by reference in its entirety for all purposes).

Exemplary systems are described in detail in, e.g., U.S. patent application Ser. No. 11/901,273, filed Sep. 14, 2007 and U.S. patent application Ser. No. 12/134,186, filed Jun. 5, 2008, the full disclosures of which are incorporated herein by reference in their entirety for all purposes.

Further, as noted above, the invention provides data processing systems for transforming sequence read data into consensus sequence data. In certain embodiments, the data processing systems include machines for generating sequence read data by interrogating a template nucleic acid molecule. In certain preferred embodiments, the machine generates the sequence read data using a sequencing-by-synthesis technology, as described elsewhere herein, but the machine may generate the sequence read data using other sequencing technologies known to those of ordinary skill in the art, e.g., pyrosequencing, ligation-mediated sequencing, Sanger sequencing, capillary electrophoretic sequencing, etc. Such machines and methods for using them are available to the ordinary practioner.

In another aspect, the invention provides data processing systems for transforming sequence read data from one or more sequencing reactions into consensus sequence data representative of an actual sequence of one or more template nucleic acids analyzed in the one or more sequencing reactions. Such data processing systems typically comprise a computer processor for processing the sequence read data according to the steps and methods described herein, and computer usable medium for storage of the initial sequence read data and/or the results of one or more steps of the transformation (e.g., the consensus sequence data), such as a computer-readable medium.

Figure 8:
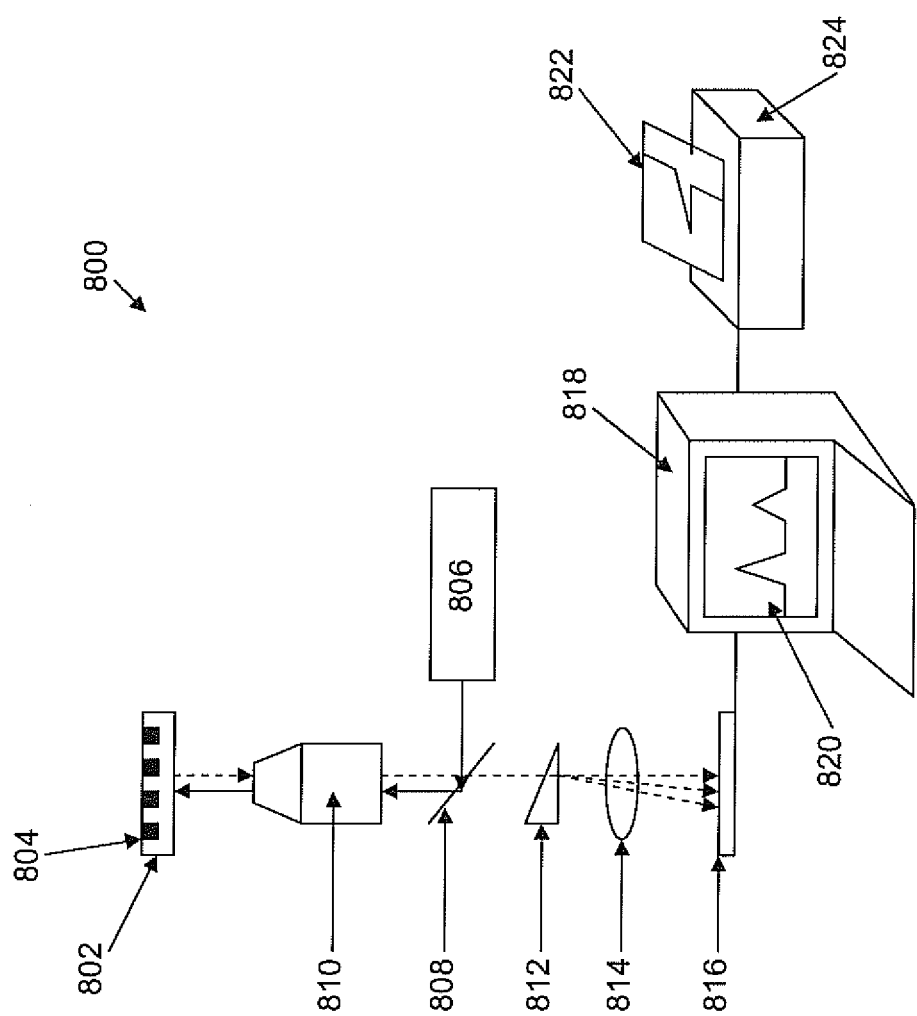
FIG. 8 shows an embodiment of a system of the invention.

As shown in FIG. 8, the system 800 includes a substrate 802 that includes a plurality of discrete sources of chromophore emission signals, e.g., an array of zero mode waveguides 804. An excitation illumination source, e.g., laser 806, is provided in the system and is positioned to direct excitation radiation at the various signal sources. This is typically done by directing excitation radiation at or through appropriate optical components, e.g., dichroic element 808 and objective lens 810, that direct the excitation radiation at the substrate 802, and particularly the array of zero mode waveguides 804. Emitted signals from the array of zero mode waveguides 804 are then collected by the optical components, e.g., objective 810, and passed through additional optical elements, e.g., dichroic element 808, prism 812 and lens 814, until they are directed to and impinge upon an optical detection system, e.g., detector array 816. The signals are then detected by detector array 816, and the data from that detection is transmitted to an appropriate data processing system, e.g., computer 818, where the data is subjected to interpretation, analysis, and ultimately presented in a user ready format, e.g., on display 820, or printout 822, from printer 824. As will be appreciated, a variety of modifications may be made to such systems, including, for example, the use of multiplexing components to direct multiple discrete beams at different locations on the substrate, the use of spatial filter components, such as confocal masks, to filter out-of focus components, beam shaping elements to modify the spot configuration incident upon the substrates, and the like (See, e.g., Published U.S. Patent Application Nos. 2007/0036511 and 2007/095119, and U.S. patent application Ser. No. 11/901,273, all of which are incorporated herein by reference in their entireties for all purposes.).

IV. Uses

In certain aspects, the subject invention provides substrates and methods for performing single-molecule observation. The optical arrays of the invention can provide information on individual molecules whose properties are hidden in the statistical mean that is recorded by ordinary ensemble measurement techniques. In addition, because of multiplexing, the arrays are conducive to high-throughput implementation, requiring small amounts of reagent(s), and taking advantage of the high bandwidth of modern avalanche photodiodes for extremely rapid data collection. Moreover, because single-molecule counting automatically generates a degree of immunity to illumination and light collection fluctuations, single-molecule analysis can provide greater accuracy in measuring quantities of material than bulk fluorescence or light-scattering techniques. As such, the subject substrates and devices may be used in a wide variety of circumstances including sequencing individual human genomes as part of preventive medicine, rapid hypothesis testing for genotype-phenotype associations, in vitro and in situ gene-expression profiling at all stages in the development of a multi-cellular organism, determining comprehensive mutation sets for individual clones and profiling in various diseases or disease stages. Other applications involve profiling of cell receptor diversity, identifying known and new pathogens, exploring diversity towards agricultural, environmental and therapeutic goals.

In preferred embodiments, the instant invention is directed to observing nucleic acid sequencing reactions, e.g., sequencing-by-incorporation reactions. In preferred embodiments, such an illuminated reaction analyzes a single molecule to generate nucleotide sequence data pertaining to that single molecule. For example, a single nucleic acid template may be subjected to a sequencing-by-incorporation reaction to generate one or more sequence reads corresponding to the nucleotide sequence of the nucleic acid template. For a detailed discussion of such single molecule sequencing, see, e.g., U.S. Pat. Nos. 6,056,661, 6,917,726, 7,033,764, 7,052,847, 7,056, 676, 7,170,050, 7,361,466, 7,416,844; Published U.S. Patent Application Nos. 2007-0134128 and 2003/0044781; and M. J. Levene, J. Korlach, S. W. Turner, M. Foquet, H. G. Craighead, W. W. Webb, SCIENCE 299:682-686, January 2003 Zero-Mode Waveguides for Single-Molecule Analysis at High Concentrations, all of which are incorporated herein by reference in their entireties for all purposes.

V. Examples

Example 1

Preparing Substrates Having High Bias Using: a) Selective Passivation, b) Functionalization of the Transparent/Silica-Based Surface, and c) Selective Removal The process described herein is applied to various types of samples including a 1) ZMW array comprising a layer of aluminum on fused silica having about 3000 apertures with diameters between about 60 nm and 130 nm; 2) mixed surface coupons having aluminum and fused silica portions, and 3) separate aluminum substrates and silicon-oxide substrates, each treated identically.

The mixed surface coupons can be, for example, fused silica having deposited onto its surface a 100 nm thick Aluminum. Substrates are patterned at the wafer level utilizing standard photolithographic techniques. The finished pattern consists of 1 mm squares evenly spaced on a fused silica substrate. Prior to aluminum deposition, the wafers are cleaned in a sulfuric and hydrogen peroxide mixture (Piranha solution) to remove organic residues from the surface.

Where the assay is done on two separate substrates treated identically, the substrates can be, for example 1) a silicon substrate with 20 nm thermally grown silicon oxide and 2) a fused silica wafer having a layer of aluminum. For the silicon substrate with thermally grown silicon oxide, silicon substrates are commercially available and are typically 1-12" diameter wafers that are approximately 500 microns thick. A 20 nm oxide is grown on the surface by high temperature oxidation in a tube furnace. In some instances, the wafer is scribed with a diamond tipped scribing tool and is broken into small pieces to enable multiple tests per wafer. To prepare the aluminum coated fused silica substrates, a 100 nm thick Aluminum film is deposited (evaporated or sputtered) on high purity fused silica was used for passivation testing. The fused silica wafers are commercially available and are typically 1-12" that are approximately 500 microns thick. Prior to aluminum deposition, the wafers are cleaned in a sulfuric and hydrogen peroxide mixture (Piranha solution) to remove organic residues from the surface.

Just prior to surface deposition, samples are plasma treated in medical grade air for about 2 minutes at a backfill pressure of 1900 mTorr. The plasma treatment removes organic residues from the surface and provides enhanced bonding for subsequent deposited molecules. Immediately following plasma treatment, the samples are placed in a pre-heated (90 C) container containing 0.5% w/v of the vinyl phosphonic acid-acrylic acid copolymer ALBRITECT CP30 (Rhodia) in water. After 2 minutes, the samples are removed from the CP30 vessel, rinsed in a stream of water, and then placed in a 90 C oven. After 10 minutes in the oven, the samples are then placed in a vessel containing biotin-peg-silane dissolved in ethanol at a concentration of 150 micromolar. After 2 hours, the samples are removed from the biotin-peg-silane vessel, rinsed in a stream of methanol, and then placed in a 90 C oven. After 10 minutes in the oven, the samples are placed in a pre-heated (90 C) vessel containing 0.5% w/v of the acidic phosphonate containing polymer AQUARITE ESL (Rhodia). After 10 minutes, the samples are removed from the AQUARITE ESL vessel, rinsed in a stream of water, and then placed in a 90 C oven for 10 minutes. The samples are then removed from the oven and either tested immediately or stored in a dessicated vacuum container for later use.

Example 2

Bead Assay for Determination of Bias by Fluorescence

Labeled latex beads (488 Oregon Green (OG)(Invitrogen)) coated with neutravidin are used as a bias probe for determining adsorption bias on a mixed surface, where one of the components (in this case, the fused silica (fusi)) is functionalized with biotin, and the other component (e.g. metal) is coated with a protein rejection agent. Neutravidin, a 53 kD tetrameric protein, forms a strong bond (Kd~10-15 mol/L) with biotin. The bead is utilized in order to visualize fluorescence on the metallic surface, which may otherwise be undetectable due to quenching.

The labeled neutravidin beads are diluted in a pH 7.5 buffer prior to sample exposure. A small droplet is then pipetted onto a two-component coupon (consisting of equal parts fused silica and metal), where the surface of the coupon has been treated to produce a bias. The droplet and coupon are placed in a humidity chamber to mitigate evaporation. After 15 minutes, the coupon is washed in Millipore or DI water and dried in a nitrogen stream. A Typhoon fluorescence scanner with a 488 laser and 520 notch filter is used to visualize amount of the labeled beads that adsorbed on the surfaces. Commercially available software packages (Image J, ImageQuant) are then used for quantification of the subsequent fluorescence on each surface component. The bias is defined as the fluorescence intensity of the fusi surface divided by the intensity at the metal surface. Bias numbers in excess of 100:1 have been regularly observed.

Figure 9:
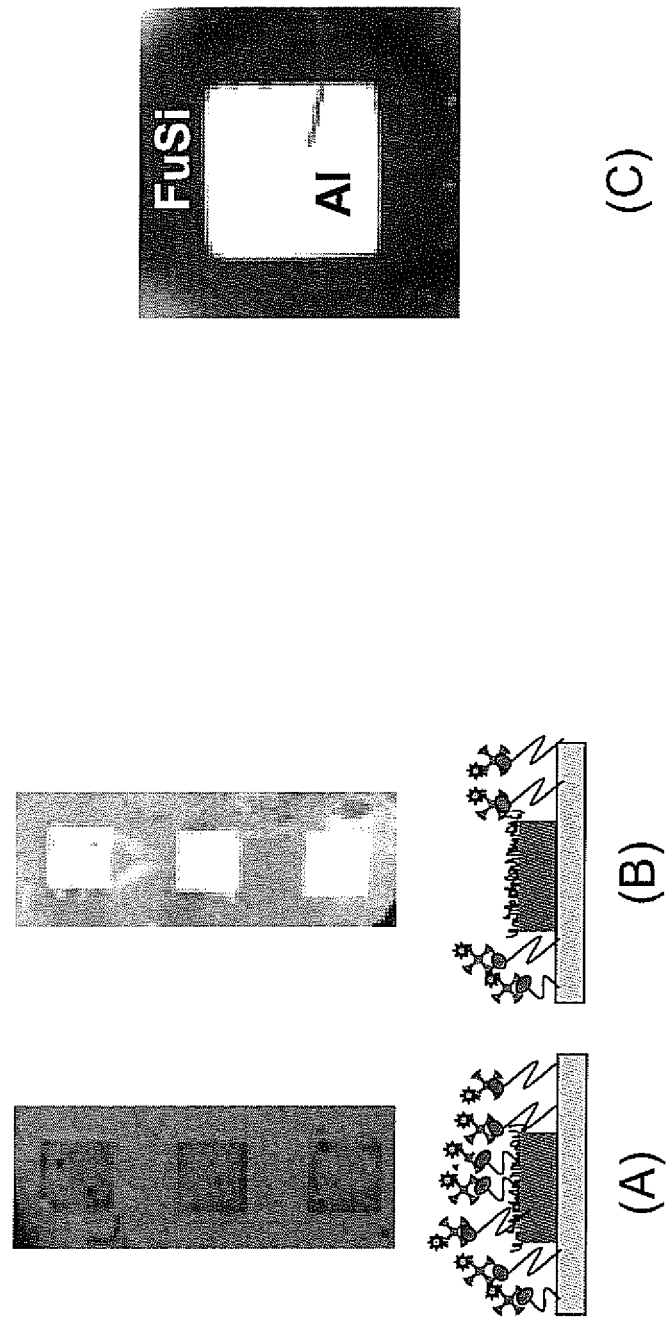
FIG. 9(A) shows a fluorescence scanner images a coupon having silica-based and metal or metal oxide regions prior to the selective removal step and a schematic illustration of the coupon at that point.
FIG. 9(B) shows a fluorescence scanner image of the coupon after the selective removal step and a schematic illustration of the coupon.
FIG. 9(C) shows a fluorescence scanner image of a coupon having a bias of greater than 100 as determined in a fluorescent bead-based assay.

Substrates treated as described in Example 1 were assayed for bias using the fluorescent neutravidin bead assay. After thorough washing, the coupon was placed on a typhoon scanner that employed a 488 laser excitation and 520 nm notch filter. FIGS. 9 (A) and (B) show Typhoon fluorescence scanner image of 488 nm-fluorescently labeled latex beads coated with neutravidin immobilized to the surface of a mixed substrate consisting of three Al squares deposited on a fused silica substrate (regions that are fluorescent appear dark in the figure). FIG. 9A (above) shows the fluorescent scanner image protein adsorption following the first two steps of the process where the surface consists of both metal passivating agent and fused silica functionalizing agent. FIG. 9A (below) shows a schematic illustration of the surface after the treatment of the substrate with silane-PEG-Biotin and before the selective removal step. FIG. 9(B) (above) shows the fluorescent scanner image after the selective removal step, demonstrating the selective removal of the functionalizing agent from the metal as evidenced by the low fluorescence (white appearance) on the Al, while the fused silica substrate retains the functionalizing reagent in order to immobilize protein. FIG. 9(B) (below) shows a schematic illustration of the substrate after the selective removal step. FIG. 9(C) shows a Typhoon fluorescence scanner image of a single square of Al deposited on the fused silica substrate (regions that are fluorescent appear dark in the figure) after the selective removal process. The bias of the coupon, defined as the ratio of fluorescence intensity on the fused silica surface to that of the Al surface, in the figure is 135:1.

Example 3

Labeled Template Assay for Determination of Bias

An alexa-488 labeled IDT-32 primer annealed to a 72base mini-circle DNA template and subsequently immobilized to phi29 DNA polymerases is used as a bias probe. The metal-oxide, atomic layer deposition (ALD) alumina is generally used in this case to mitigate metal fluorescence quenching.

The labeled primer/template complex is immobilized to DNA polymerase in a DNA low-bind tube in a suitable buffer for 15 minutes prior to sample exposure. A small droplet is then pipetted onto a two-component coupon (consisting of equal parts fusi and metal-oxide), where the surface of the coupon has been treated. The droplet and coupon are placed in a humidity chamber to mitigate evaporation. After 15 minutes, the coupon is washed in Millipore or DI water and dried in a nitrogen stream. A Typhoon fluorescence scanner with a 488 laser and 520 notch filter is used to visualize amount of protein that adsorbed on the surfaces. Commercially available software packages (Image J, ImageQuant) are used for quantification of the subsequent fluorescence on each surface component. The bias is defined as the fluorescence intensity of the fusi surface divided by the intensity at the metal surface. Bias numbers in excess of 10:1 and in some cases, 100:1 have been observed for surfaces prepared as described herein.

Example 4

Assay for the Specificity of Biotin-Neutravidin Binding

488 OG (Invitrogen) labeled neutravidin is used as a specificity probe. To quantify the specificity of immobilization to surfaces functionalized with biotin, such as the transparent or silica-based surface, blocked neutravidin can be used. Blocked neutravidin is produced by mixing neutravidin in a concentrated biotin buffer solution (1 uM biotin, pH7.5). As a result, the blocked neutravidin binding sites are filled prior to exposure to the biotinylated surface. The specificity of immobilization is determined by measuring the ratio fluorescent signal from portions of the surface treated with unblocked and biotin-blocked neutravidin.

Equal volumes of unblocked and biotin blocked neutravidin are diluted to 35 nM in pH7.5 buffer. One small droplet of each solution (blocked/unblocked) is then pipetted in close proximity onto a fused silica coupon, where the surface of the coupon has been treated. The droplets and coupon are placed in a humidity chamber to mitigate evaporation. After 15 minutes, the coupon is washed in Millipore or DI water and dried in a nitrogen stream. A Typhoon fluorescence scanner with a 488 laser and 520 notch filter is used to visualize amount of protein that adsorbed on the surfaces. Commercially available software packages (Image J, ImageQuant) are used for quantification of the subsequent fluorescence on each surface component. The specificity is defined as the fluorescence intensity of the unblocked portion of the neutravidin surface divided by the intensity of the biotin-blocked portion of the neutravidin surface. Specificity numbers in excess of 100:1 have been measured for the surfaces prepared as described herein.

Example 5

Assay for Bias by Ellipsometry

Immobilization bias is confirmed by measurements of the ellipsometric thickness of the adsorbed protein layers on the two different surfaces, each treated identically. Because the ellipsometry measurement requires a relatively large area, in some cases, separate silica-based and metal or metal oxide based samples are treated identically and used. A variable angle spectroscopic ellipsometer (VASE) (J. Wollam) is used to assess changes in thickness due to protein immobilization (e.g. neutravidin or streptavidin) on a silicon dioxide surface and aluminum surface. The ellipsometric bias is defined as the change in thickness on the silicon oxide surface divided by the change in thickness on the aluminum oxide surface ($\Delta d_{Si}/\Delta d_{Al}$).

Commercially available neutravidin (MW~60 kD) is used as the protein assay probe due to its high specificity to biotin. Stock concentrations of neutravidin are diluted to 30 nM in pH7.5 MOPS buffer and vortexed thoroughly. An 8 uL aliquot of the dilute neutravidin reagent is pipetted onto a surface prepared in the methods described above. The samples are then placed in a humidity chamber to mitigate evaporation. After 15 minutes the sample is removed and rinsed in a stream of nanopure water and then dried in a nitrogen stream. The samples were then mounted on the VASE and psi and delta values were acquired across the visible wavelength range (400 to 700 nm). A four layer model is employed to correlate psi and delta to film thicknesses which included the ambient (air), protein layer, oxide, and metal. Dielectric constants are input from literature values (Palik). Example ellipsometric bias results are shown in FIG. 10.

Figure 10:
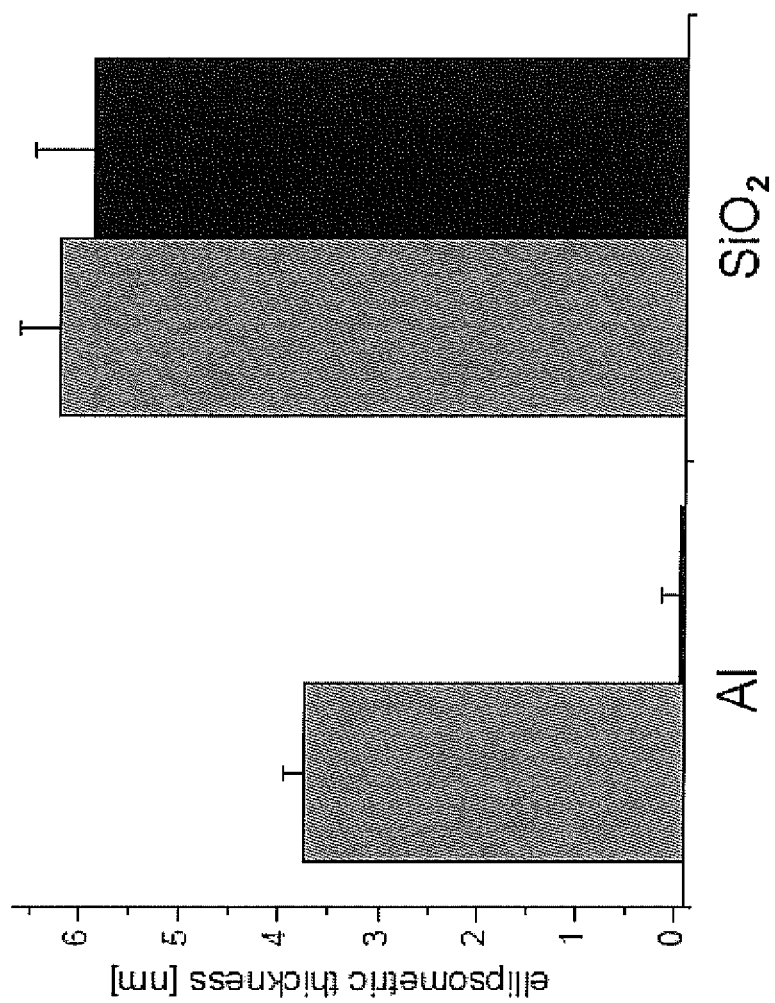
FIG. 10 shows data for ellipsometric thickness, demonstrating high bias.

In FIG. 10, the gray columns represent the measured ellipsometric thickness on the Al and SiO2 surface regions before passivation, indicating a significant amount of binding of the neutravidin to the aluminum surface. The dark columns in FIG. 10 represent the measured ellipsometric thickness of the Al and SiO2 surfaces after treatment by a method of the invention. It can be seen that after the treatment, very little of the neutravidin was on the Al surface, while the amount bound to the SiO2 surface is very similar to the amount bound prior to treatment. The ellipsometric bias can be quantified, for example, by taking the ratio of the dark columns. For the experiment shown in FIG. 10, ellipsometric bias was determined to be about 60.

Example 6

Bias by XPS

Coupons of fused silica having regions of aluminum deposited thereon were treated as described in Example 1. Phosphonate deposition on aluminum was confirmed by X-ray photoelectron spectroscopy by the presence of peaks attributable to phosphorous. In this method, the passivation bias (defined here as the ratio of the atom % of individual components to a metal passivating molecule (e.g. atom % of P from CP30) from the metal and glass surfaces, respectively (% $P_{Al}$:% $P_{fusi}$)), can be qualitatively assessed. Measurements showed that the % P on Al was 10% and was <0.02% on fusi (below detection limit)

Example 8

Observation of DNA Polymerase Activity—Single Molecule Sequencing

Figure 11:
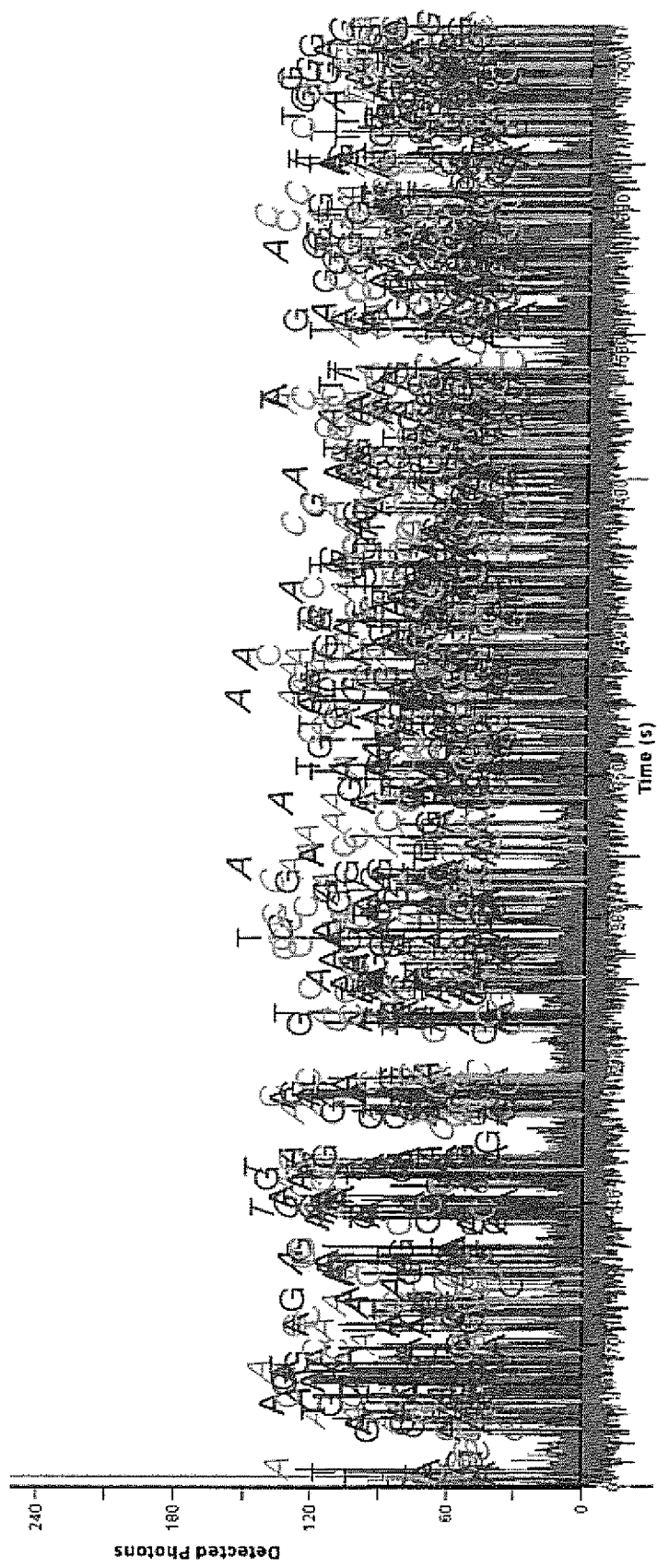
FIG. 11 shows a data trace for a four-color single-molecule sequencing reaction performed on a ZMW array produced as described herein.

A zero-mode waveguide array having about 3000 apertures through a 100 nm layer of Al on fused silica is treated as described in Example 1. Prior to sequencing, a single DNA polymerase molecule having a biotin label is complexed with a double stranded and primed DNA to form a polymerase-template-primer complex. This complex is immobilized on the biotin functionalized fused silica substrate of the zero-mode waveguide using streptavidin or neutravidin. A sequencing reaction was carried in the manner described in Eid et al. Science, 323, 134-138 (2009). The zero-mode waveguide array was exposed to a solution comprising labeled nucleotide bases. Each base was labeled with a unique fluorescent marker (organic dye) that served as signatures for detection, 555-T, 568-G, 647-A and Cy5.5-C. Following immobilization of the DNA polymerase/template complex, the four bases were added in equal concentrations in buffer were added to the system along with manganese to catalyze the reaction. The fluorophores were excited by 532 nm and 641 nm lasers. Fluorescence emission was monitored using a cooled CCD camera and the time averaged spectra were converted to trace data acquired prior to data acquisition. FIG. 11 shows a portion of a data trace from the single molecule real-time four-color sequencing reaction in a zero-mode waveguide. The data has been analyzed using base calling software in order to correlate the observed peaks with the labeled bases that comprise DNA, (A) adenine, (C) cytosine, (G) guanine and (T) thymine.

Several aspects of the sequencing system were markedly improved by employing surfaces prepared by the methods described above as compared to surfaces prepared in other ways, including lower surface stickiness (lower background (non-sequencing related) fluorescent signal), higher sequencing yield of statistically significant sequencing and higher overall sequencing accuracy. An experiment was performed in which single molecule sequencing reactions were carried out using a zero-mode-waveguide treated by a method of the invention, and the results were compared to sequencing reactions identically performed on a surface treated in another manner, referred to herein as a PDMS treated surface. PDMS surfaces were produced through repetitive steps of deposition poly dimethyl siloxane source and subsequent oxygen plasma treatment. The result of the PDMS process is a ZMW array that is passivated with a thin layer of SiOx. As compared to the PDMS treated ZMW, fluorophore stickiness decreased by 7× as compared with PDMS passivated surfaces. The decrease in stickiness may be due to the specific attachment of the DNA polymerase do the bottom of the ZMWs in conjunction with the passivation of the aluminum oxide surface.

In addition, yields of statistically significant sequencing increased by 12× when directly compared with PDMS passivated surfaces. In some cases a 40× increase in yield has been demonstrated. The yield improvements are believed to be due to several factors: (1) The biased surface enables a higher percentage of ZMWs to be loaded in the detection volume of the zero-mode waveguide (models predict a limit of 13% for PDMS and 37% for the surface described above having high bias). (2) The biased surface enables sequencing polymerases to be located at the fused-silica ZMW bottom where excitation and emission electric fields are optimal, thus yielding higher average signal-to-noise traces. (3) The decrease in stickiness enables higher accuracy and thus higher yields of significant sequencing. (4) The specific attachment via a flexible linker enables a native conformation of DNA polymerase.

Also, sequencing readlengths were improved ~2× when directly compared with PDMS passivated surfaces. In some cases a 25× improvement has been demonstrated. The readlength improvements can be attributed part to: (1) the use of lower laser powers which is afforded by the biased surface described herein, and (2) the specific attachment at the bottom of the ZMWs reduces the instances of desorbed polymerases present when there is non-specific attachment.

It is to be understood that the above description is intended to be illustrative and not restrictive. It readily should be apparent to one skilled in the art that various embodiments and—modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

What is claimed is:

1. A method for selectively functionalizing a surface of a substrate having both silica-based portions and metal or metal oxide portions comprising:
   a) exposing a surface of a substrate having both silica-based portions and metal or metal oxide portions to an agent that preferentially binds to the metal or metal oxide portions to produce passivated metal or metal oxide portions of the surface;
   b) exposing the surface of the substrate to a silica functionalizing agent that binds to both the silica-based portions and the passivated metal or metal oxide portions of the surface, then rinsing the surface of the substrate; and
   c) after step b), exposing the silica-based portions and the passivated metal or metal oxide portions of the surface of the substrate to a selective removal compound that preferentially removes the silica functionalizing agent from the passivated metal or metal oxide portions of the surface.

2. The method of claim 1 wherein the agent that preferentially binds to the metal or metal oxide portions comprises phosphate or phosphonate functionality.

3. The method of claim 1 wherein the silica functionalizing agent comprises a silane coupling agent.

4. The method of claim 1 wherein the selective removal compound comprises an acidic compound.

5. The method of claim 1 wherein the selective removal compound comprises a compound having a pK$_a$ of less than 6.

6. The method of claim 1 wherein the selective removal compound comprises a polymer.

7. The method of claim 6 wherein the polymer comprises carboxylate, sulfonate, sulfate, phosphonate or phosphate functionality.

8. The method of claim 6 wherein the polymer comprises a homopolymer or copolymer of one or more of the monomers vinyl(acrylic acid), vinyl(sulfonic acid), vinyl(phosphonic acid), vinyl(styrenesulfonic acid), maleic acid, or salts thereof.

9. The method of claim 6 wherein the polymer comprises poly(vinylsulfonic acid) or

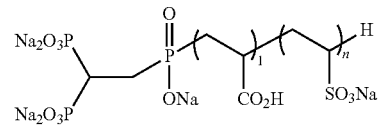

where m is about 24 and n is about 16.

10. The method of claim 1 wherein the silica-based portions comprise optical confinement regions.

11. The method of claim 1 wherein the substrate comprises an array of optical confinement regions wherein the silica-based portions comprise bases of apertures though a metal or metal oxide layer on a transparent silica-based substrate.

12. A method for selectively functionalizing a surface of a substrate having both silica-based portions and metal or metal oxide portions comprising;
   a) treating a surface of a substrate having both silica-based portions and metal or metal oxide portions with a compound comprising phosphate or phosphonate groups to produce passivated metal or metal oxide portions of the surface;
   b) treating the surface of the substrate with a silica functionalizing agent that binds to both the silica-based and the passivated metal or metal oxide portions of the surface; and
   c) treating the surface of the substrate with an acidic compound having a pK$_a$ of less than 6 to remove silica functionalizing agent from the passivated metal or metal oxide portions of the surface.

13. A method for attaching a desired molecule to a silica-based portion of a surface of a substrate having both silica-based portions and metal or metal oxide portions comprising;
   a) exposing a surface of a substrate having both silica-based portions and metal or metal oxide portions to an agent that preferentially binds to the metal or metal oxide portions to produce passivated metal or metal oxide portions of the surface;
   b) exposing the surface of the substrate to a coupling agent that binds to both the silica-based portions and the passivated metal or metal oxide portions of the surface, then rinsing the surface of the substrate;
   c) after step b), exposing the silica-based portions and the passivated metal or metal oxide portions of the surface of the substrate to a selective removal compound that preferentially removes the coupling agent from the passivated metal or metal oxide portions of the surface; and
   d) attaching the desired molecule to the coupling agent bound to the silica-based portions of the surface.

14. A method for attaching a desired molecule to a silica-based portion of a surface of a substrate having both silica-based portions and metal or metal oxide portions comprising;
   a) treating a surface of a substrate having both silica-based portions and metal or metal oxide portions with a compound comprising phosphate or phosphonate groups to produce passivated metal or metal oxide portions of the surface;
   b) treating the surface of the substrate with a coupling agent that binds to both the silica-based and the passivated metal or metal oxide portions of the surface;
   c) treating the surface of the substrate with an acidic compound having a $pK_a$ of less than 6 to remove coupling agent from the passivated metal or metal oxide portions of the surface; and
   d) attaching the desired molecule to the coupling agent bound to the silica-based portions of the surface.

15. The method of claim 12 wherein the silica functionalizing agent comprises a silane coupling agent.

16. The method of claim 12 wherein the acidic compound comprises a polymer.

17. The method of claim 16 wherein the polymer comprises carboxylate, sulfonate, sulfate, phosphonate or phosphate functionality.

18. The method of claim 16 wherein the polymer comprises a homopolymer or copolymer of one or more of the monomers vinyl(acrylic acid), vinyl(sulfonic acid), vinyl (phosphonic acid), vinyl(styrenesulfonic acid), maleic acid, or salts thereof.

19. The method of claim 16 wherein the polymer comprises poly(vinylsulfonic acid) or

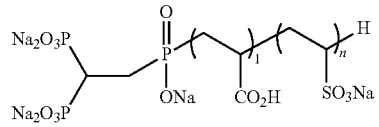

where m is about 24 and n is about 16.

20. The method of claim 12 wherein the silica-based portions comprise optical confinement regions.

21. The method of claim 12 wherein the substrate comprises an array of optical confinement regions wherein the silica-based portions comprise bases of apertures though a metal or metal oxide layer on a transparent silica-based substrate.

* * * * *